US011905563B2

(12) United States Patent
Rigoutsos et al.

(10) Patent No.: US 11,905,563 B2
(45) Date of Patent: Feb. 20, 2024

(54) LEVERAGING THE PRESENCE OR ABSENCE OF MIRNA ISOFORMS FOR RECOMMENDING THERAPY IN CANCER PATIENTS

(71) Applicant: THOMAS JEFFERSON UNIVERSITY, Philadelphia, PA (US)

(72) Inventors: Isidore Rigoutsos, Philadelphia, PA (US); Aristeidis G. Telonis, Philadelphia, PA (US)

(73) Assignee: Thomas Jefferson University, Philadelphia, PA (US)

( * ) Notice: Subject to any disclaimer, the term of this patent is extended or adjusted under 35 U.S.C. 154(b) by 879 days.

(21) Appl. No.: 16/343,256

(22) PCT Filed: Oct. 23, 2017

(86) PCT No.: PCT/US2017/057909
§ 371 (c)(1),
(2) Date: Apr. 18, 2019

(87) PCT Pub. No.: WO2018/076015
PCT Pub. Date: Apr. 26, 2018

(65) Prior Publication Data
US 2019/0249262 A1 Aug. 15, 2019

Related U.S. Application Data

(60) Provisional application No. 62/502,133, filed on May 5, 2017, provisional application No. 62/441,837, filed on Jan. 3, 2017, provisional application No. 62/411,417, filed on Oct. 21, 2016.

(51) Int. Cl.
| | |
|---|---|
| *C12Q 1/6886* | (2018.01) |
| *G01N 1/30* | (2006.01) |
| *G01N 33/50* | (2006.01) |
| *G16B 40/00* | (2019.01) |
| *G16B 40/20* | (2019.01) |
| *G16B 40/30* | (2019.01) |
| *G16H 50/30* | (2018.01) |
| *G16H 50/20* | (2018.01) |
| *G16B 25/00* | (2019.01) |
| *G16B 25/10* | (2019.01) |
| *G16H 50/70* | (2018.01) |

(52) U.S. Cl.
CPC .......... *C12Q 1/6886* (2013.01); *G01N 1/30* (2013.01); *G01N 33/50* (2013.01); *G16B 40/00* (2019.02); *G16B 40/20* (2019.02); *G16B 40/30* (2019.02); *G16H 50/20* (2018.01); *G16H 50/30* (2018.01); *C12Q 2600/106* (2013.01); *C12Q 2600/112* (2013.01); *C12Q 2600/118* (2013.01); *C12Q 2600/156* (2013.01); *C12Q 2600/158* (2013.01); *C12Q 2600/178* (2013.01); *G16B 25/00* (2019.02); *G16B 25/10* (2019.02); *G16H 50/70* (2018.01)

(58) Field of Classification Search
CPC ........ G16H 50/30; G16H 50/20; G16B 40/00; G16B 40/30; G16B 40/20; G01N 1/30; G01N 33/50; C12Q 1/6886
See application file for complete search history.

(56) References Cited

FOREIGN PATENT DOCUMENTS

| WO | 2014179765 A2 | 11/2014 | | |
|---|---|---|---|---|
| WO | WO-2014179765 A2 | * | 11/2014 | ........... C12Q 1/6886 |

OTHER PUBLICATIONS

Li et al. BMC Genomics 2012 13(suppl 1): S13 (Year: 2012).*
Aalto, A.P., et al., "Small non-coding RNAs mount a silent revolution in gene expression", Current Opinion in Cell Biology, vol. 24, No. 3, pp. 333-340, 2012.
Backes, C., et al., "miRPathDB: a new dictionary on microRNAs and target pathways", Nucleic Acids Research, vol. 45, pp. D90-D96, 2016.
Bandiera, S., et al., "miR-122-a key factor and therapeutic target in liver disease", Journal of Hepatology, vol. 62, pp. 448-457, 2015.
Barroso-Del Jesus, A., et al., "The miR-302-367 cluster as a potential sternness regulator in ESCs", Cell Cycle, No. 8, No. 3, pp. 394-398, 2009.
Bartel, D.P., "MicroRNAs: genomics, biogenesis, mechanism, and function", Cell, vol. 116, pp. 281-297, 2004.
Bartel, D.P., "MicroRNAs: target recognition and regulatory functions", Cell, vol. 136, pp. 215-233, 2009.
Boele, J., et al., "PAPD5-mediated 3' adenylation and subsequent degradation of miR-21 is disrupted in proliferative disease", Proceedings of the National Academy of Sciences of the USA, vol. 111, No. 31, pp. 11467-11472, 2014.
Calin, G.A., et al., "MicroRNA signatures in human cancers", Nature Reviews Cancer, vol. 6, pp. 857-866, 2006.
Cancer Genome Atlas Network, "Comprehensive molecular characterization of human colon and rectal cancer", Nature, vol. 487, No. 7407, pp. 330-337, 2012.
Chu, A., "Large-scale profiling of microRNAs for The Cancer Genome Atlas", Nucleic Acids Research, vol. 44, No. 1, e3, 2016.
Clark, M.B., et al., "The dark matter rises: the expanding world of regulatory RNAs", Essays in Biochemistry, vol. 54, pp. 1-16, 2013.
Clerget, G., et al., "Small non-coding RNAs: a quick look in the rearview mirror", Methods in Molecular Biology, vol. 1296, pp. 3-9, 2015.

(Continued)

*Primary Examiner* — Jerry Lin
(74) *Attorney, Agent, or Firm* — Cozen O'Connor

(57) ABSTRACT

A method of identifying a subject in need of therapeutic intervention to treat a disease or condi-tion or disease recurrence or disease progression comprising, isolating isomiRs or miRNAs from a sample obtained from the subject; and characterizing the isomiRs or miRNAs and their presence or absence in the sample to identify a signature, wherein when the signature is indicative of a di-agnosis of the disease then treatment of the subject is recommended.

62 Claims, 23 Drawing Sheets
Specification includes a Sequence Listing.

(56) References Cited

OTHER PUBLICATIONS

Coolen, M., et al., "miR-9: a versatile regulator of neurogenesis", Frontiers in Cellular Neuroscience, vol. 7, No. 220, pp. 1-11, 2013.
Cortez, M.A., et al., "MicroRNAs in body fluids-the mix of hormones and biomarkers", Nature Reviews Clinical Oncology, vol. 8, No. 8, pp. 467-477, 2011.
Di Leva, G., et al., "MicroRNAs in cancer", Annual Review of Pathology, vol. 9, pp. 287-314, 2014.
Dumortier, O., et al., "Shaping and preserving beta-cell identity with microRNAs" Diabetes, Obesity & Metabolism, vol. 18, Suppl 1, pp. 51-57, 2016.
Edelstein, L.C., et al., "MicroRNAs in platelet production and activation", Journal of Thrombosis and Haemo-stasis: JTH, vol. 11, Suppl 1, pp. 340-350, 2013.
Flowers, et al., "MicroRNAs associated with exercise and diet: a systematic review", Physiological Genomics, vol. 47, pp. 1-11, 2015.
Gao, Z., et al., "The miR-302/367 cluster: a comprehensive update on its evolution and functions", Open Biology, vol. 5, No. 150138, 7 pages, 2015.
Goswami, R., et al., "Optimization and analysis of a quantitative real-time PCR-based technique to determine microRNA expression in formalin-fixed paraffin-embedded samples", BMC Biotechnology, vol. 10, No. 47, pp. 1-12, 2010.
Guyon, I., et al., "Gene Selection for Cancer Classification using Support Vector Machines", Machine Learning, vol. 46, Issue 1-3, pp. 389-422, 2002.
Ha, M., et al., "Regulation of microRNA biogenesis", Nature Reviews Molecular Cell Biology, vol. 15, pp. 509-524, 2014.
Hilz, A., et al., "The roles of microRNAs and siRNAs in mammalian spermatogenesis", Development, vol. 143, No. 17, pp. 3061-3073, 2016.
Honda, S., et al., "Dumbbell-PCR: a method to quantify specific small RNA variants with a single nucleotide resolution at terminal sequences", Nucleic Acids Research, vol. 43, No. 12, e77, 12 pages, 2015.
Hood, L., et al., "The Human Genome Project: big science transforms biology and medicine", Genome Medicine, vol. 5, No. 79, 8 pages, 2013.
Hornick, N.I., et al., "Serum Exosome MicroRNA as a Minimally-Invasive Early Biomarker of AML", Scientific reports, vol. 5, No. 11295, 11 pages, 2015.
Judish, L.I., et al., "miR-219 regulates neural progenitors by dampening apical Par protein-dependent Hedgehog signaling", Development, vol. 143, pp. 2292-2304, 2016.
Jeon, T.I., et al., "miRNA and cholesterol homeostasis", Biochimica et Biophysica Acta, vol. 1861, No. 12 Pt B, pp. 2041-2046, 2016.
Koppers-Lalic, D., et al., "Nontemplated nucleotide additions distinguish the small RNA composition in cells from exosomes", Cell Reports, vol. 8, pp. 1649-1658, 2014.
Koppers-Lalic, D., et al., "Non-invasive prostate cancer detection by measuring miRNA variants (isomiRs) in urine extracellular vesicles", Oncotarget, vol. 7, No. 16, pp. 22566-22578, 2016.
Kumar, P., et al., "miR-ID: a novel, circularization-based platform for detection of microRNAs", RNA, vol. 17, pp. 365-380, 2011.
Landgraf, P., et al., "A mammalian microRNA expression atlas based on small RNA library sequencing", Cell, vol. 129, pp. 1401-1414, 2007.
Lee, et al., "The C. elegans heterochronic gene lin-4 encodes small RNAs with antisense complementarity to lin-14", Cell, vol. 75, No. 5, pp. 843-854, 1993.
Loher, P., et al., "IsomiR Expression Profiles in Human Lymphoblastoid Cell Lines Exhibit Population and Gender Dependencies", Oncotarget, vol. 5, No. 18, pp. 8790-8802, 2014.
Londin, E., et al., "Analysis of 13 cell types reveals evidence for the expression of numerous novel primate- and tissue-specific microRNAs", Proceedings of the National Academy of Sciences of the USA, vol. 112, No. 10, pp. E1106-E1115, 2015.
Lu, J., et al., "MicroRNA expression profiles classify human cancers", Nature, vol. 435, No. 7043, pp. 834-838, 2005.

McCall, M.N., et al., "The Gene Expression Barcode 3.0: improved data processing and mining tools", Nucleic Acids Research, vol. 42, pp. D938-D943, 2014.
McHardy, A.C., et al., "Accurate phylogenetic classification of variable-length DNA fragments", Nature Methods, vol. 4, No. 1, pp. 63-72, 2007.
Mehta, R., et al., "Circulating miRNA in patients with non-alcoholic fatty liver disease and coronary artery disease", BMJ Open Gastroenterology, vol. 3, No. e000096, 7 pages, 2016.
Mogilyansky, E., et al., "The miR-17/92 cluster: a comprehensive update on its genomics, genetics, functions and Increasingly important and numerous roles in health and disease", Cell Death and Differentiation, vol. 20, pp. 1603-1614, 2013.
Noble, W.S., "What is a support vector machine?", Nature Biotechnology, vol. 24, No. 12, pp. 1565-1567, 2006.
Pimental, F., et al., "Technology in MicroRNA Profiling: Circulating MicroRNAs as Noninvasive Cancer Biomarkers in Breast Cancer", Journal of Laboratory Automation, vol. 20, No. 5, pp. 574-588, 2014.
Reinhart, B.J., et al., "The 21-nucleotide let-7 RNA regulates developmental timing in Caenorhabditis elegans", Nature, vol. 403, 901-906, 2000.
Rosenfeld, N., et al., "MicroRNAs accurately identify cancer tissue origin", Nature Biotechnology, vol. 26, No. 4, pp. 462-469, 2008.
Salem, O., et al., "The highly expressed 5'isomiR of hsa-miR-140-3p contributes to the tumor-suppressive effects of miR-140 by reducing breast cancer proliferation and migration", BMC Genomics, vol. 17, No. 566, 16 pages, 2016.
Schaefer, M.H., et al., "Cell type-specific properties and environment shape tissue specificity of cancer genes", Scientific Reports, vol. 6, No. 20707, 14 pages, 2016.
Schirle, N.T., et al., "Structural basis for microRNA targeting", Science, vol. 346, No. 6209, pp. 608-613, 2014.
Shi, J. "Considering Exosomal miR-21 as a Biomarker for Cancer", Journal of Clinical Medicine, vol. 5, No. 42, 12 pages, 2016.
Shmulevich, I., et al., "Binary analysis and optimization-based normalization of gene expression data", Bioinformatics, vol. 18, No. 4, pp. 555-565, 2002.
Sparks, E., et al., "Spatiotemporal signalling in plant development", Nature Reviews Genetics, vol. 14, No. 9, pp. 631-644, 2013.
Starega-Roslan, J., et al., "Sequence features of Drosha and Dicer cleavage sites affect the complexity of isomiRs," International Journal of Molecular Sciences, vol. 16, pp. 8110-8127, 2015.
Statnikov, A., et al., "A comprehensive comparison of random forests and support vector machines for microarray-based cancer classification", BMC Bioinformatics, vol. 9, No. 319, 10 pages, 2008.
Su, K., et al., "Diagnostic and prognostic value of plasma microRNA-195 in patients with non-small cell lung cancer", World Journal of Surgical Oncology, vol. 14, No. 224, 6 pages, 2016.
Tan, G.C, Chan, E., Molnar, A., Sarkar, R., Alexieva, D., Isa, I.M., Robinson, S., Zhang, S., Ellis, P., Langford, C.F. et al. (2014) 5' isomiR variation is of functional and evolutionary importance. Nucleic acids research, 42, pp. 9424-9435, 2014.
Telonis, A.G., et al., "Beyond the one-locus-one-miRNA paradigm: microRNA isoforms enable deeper insights into breast cancer heterogeneity", Nucleic Acids Research, vol. 43, No. 19, pp. 9158-9175, 2015.
Telonis, A.G., et al., "Knowledge about the presence or absence of miRNAisoforms (isomiRs) can successfully discriminate amongst 32 TCGA cancer types", Nucleic Acids Research, vol. 45, No. 6, pp. 2973-2985, 2017.
Tsirigos, A., et al., "A sensitive, support-vector-machine method for the detection of horizontal gene transfers in viral, archaeal and bacterial genomes", Nucleic Acids Research, vol. 33, No. 12, pp. 3699-3707, 2005.
Tuna, S., et al., "Classification with binary gene expressions". Journal of Biomedical Science and Engineering, vol. 2, No. 6, pp. 390-399, 2009.
Veneziano, D., et al., "Noncoding RNA: Current Deep Sequencing Data Analysis Approaches and Challenges", Human Mutation, vol. 37, No. 12, pp. 1283-1298, 2016.

(56) References Cited

OTHER PUBLICATIONS

Volnia, S., et al., "A microRNA expression signature of human solid tumors defines cancer gene targets", Proceedings of the National Academy of Sciences of the USA, vol. 103, No. 7, pp. 2257-2261, 2006.

Volloch, V., et al., "Antisense globin RNA in mouse erythroid tissues: Structure, origin, and possible function", Proceedings of the National Academy of Sciences of the USA, vol. 93, pp. 2476-2841, 1996.

Wang, Y., et al., "Identification of miRNAs as potential new biomarkers for nervous system cancer", Tumour biology: The Journal of the International Society for Oncodevelopmental Biology and Medicine, vol. 35, No. 11, pp. 11631-1163, 2014.

Warnecke, F., et al., "Metagenomic and functional analysis of hindgut microbiota of a wood-feeding higher termite", Nature, vol. 450, No. 7169, pp. 560-565, 2007.

Winter, J., et al., "Many roads to maturity: microRNA biogenesis pathways and their regulation", Nature Cell Biology, vol. 11, No. 3, pp. 228-234, 2009.

Wojcicka, A., et al., "Next generation sequencing reveals microRNA isoforms in liver cirrhosis and hepatocellular carcinoma", The International Journal of Biochemistry & Cell Biology, vol. 53, pp. 208-217, 2014.

Xin, H., et al., "Blood-based multiple-microRNA assay displays a better diagnostic performance than single-microRNA assay in the diagnosis of breast tumor", Tumour Biology: The Journal of the International Society for Oncodevelopmental Biology and Medicine, vol. 35, No. 12, pp. 12635-12643, 2014.

Yang, Z.R., "Biological applications of support vector machines", Briefings in Bioinformatics, vol. 5, No. 4, pp. 328-338, 2004.

Yuva-Aydemir, Y., et al., "MicroRNA-9: functional evolution of a conserved small regulatory RNA", RNA Biology, vol. 8, No. 4, pp. 557-564, 2011.

Zilliox, M.J., et al., "A gene expression barcode for microarray data", Nature Methods, vol. 4, No. 11, pp. 911-913, 2007.

International Search Report dated Jan. 4, 2018 in International Application No. PCT/US2017/057909.

* cited by examiner

FIG. 7

| Cancer: | AC TGCT | THYM | READ AD | KIHC | THCA | COAD | LUAD | LUSC | HNSC | CESC | UCEC | UCS | PAAD | LGG | STAD | PCPG | UVM | SKCM | BLCA | BRCA | MESO | LIHC | PRAD | DLBC | KIRC | CHOL | ESCA | KIRP | OV | SARC | LAML | Sample # |
|---|---|---|---|---|---|---|---|---|---|---|---|---|---|---|---|---|---|---|---|---|---|---|---|---|---|---|---|---|---|---|---|---|
| miR-202-5p\|0\|-1-1 | 0 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 195 |
| miR-202-5-\|0\|-2 | 0 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 137 |
| miR-202-5p\|0\|0 | 0 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 132 |
| miR-202-5p\|-1/-1 | 0 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 114 |
| miR-202-5p\|0\|+1 | 0 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 106 |
| miR-202-3p\|-1\|0 | 0 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 0 | 1 | 1 | 1 | 1 | 211 |
| miR-202-5p\|0\|-3 | 0 | 1 | 1 | 1 | 1 | 1 | 1 | 1 | 1 | 1 | 1 | 1 | 1 | 1 | 1 | 0 | 1 | 1 | 1 | 1 | 1 | 1 | 1 | 1 | 1 | 1 | 1 | 1 | 1 | 1 | 1 | 92 |
| miR-202-3p\|0\|+1 | 0 | 1 | 1 | 1 | 1 | 1 | 1 | 1 | 1 | 1 | 1 | 1 | 1 | 1 | 1 | 0 | 1 | 1 | 1 | 1 | 1 | 1 | 1 | 1 | 1 | 1 | 0 | 1 | 1 | 1 | 1 | 247 |
| mir-202\|10\|-\|135061041\|135062 | 0 | 1 | 1 | 1 | 1 | 1 | 1 | 1 | 1 | 1 | 1 | 1 | 1 | 1 | 1 | 0 | 1 | 1 | 1 | 1 | 1 | 1 | 1 | 1 | 1 | 1 | 0 | 1 | 1 | 1 | 1 | 179 |
| miR-509-3p\|0\|-1 | 0 | 0 | 1 | 1 | 1 | 1 | 1 | 1 | 1 | 1 | 1 | 1 | 1 | 1 | 1 | 1 | 1 | 0 | 1 | 1 | 1 | 1 | 1 | 1 | 1 | 1 | 0 | 1 | 1 | 1 | 1 | 597 |
| miR-508-5p\|0\|0 | 0 | 1 | 1 | 1 | 1 | 1 | 1 | 1 | 1 | 1 | 1 | 1 | 1 | 1 | 1 | 1 | 0 | 1 | 0 | 1 | 1 | 1 | 1 | 1 | 1 | 1 | 0 | 1 | 1 | 1 | 1 | 601 |
| miR-503-5p\|0\|-1 | 0 | 1 | 1 | 1 | 1 | 1 | 1 | 1 | 1 | 1 | 1 | 1 | 1 | 1 | 1 | 1 | 0 | 1 | 0 | 1 | 1 | 1 | 1 | 0 | 1 | 1 | 1 | 1 | 0 | 1 | 1 | 591 |
| miR-509-3p\|0\|-2 | 0 | 1 | 1 | 1 | 1 | 0 | 0 | 1 | 1 | 1 | 1 | 1 | 1 | 1 | 1 | 0 | 1 | 1 | 0 | 1 | 1 | 1 | 1 | 1 | 1 | 1 | 0 | 1 | 1 | 1 | 1 | 526 |
| miR-508-3p\|0\|-2 | 0 | 0 | 1 | 1 | 1 | 0 | 1 | 1 | 1 | 1 | 1 | 1 | 1 | 1 | 1 | 0 | 0 | 1 | 0 | 1 | 1 | 1 | 1 | 1 | 1 | 1 | 0 | 1 | 1 | 1 | 1 | 470 |
| miR-509-3p\|0\|+1 | 0 | 0 | 1 | 1 | 1 | 1 | 1 | 1 | 1 | 1 | 1 | 1 | 1 | 1 | 1 | 0 | 1 | 1 | 0 | 1 | 1 | 1 | 1 | 1 | 1 | 1 | 0 | 1 | 1 | 1 | 1 | 1129 |
| miR-509-3p\|+2\|+1 | 0 | 1 | 1 | 1 | 1 | 1 | 0 | 1 | 1 | 0 | 0 | 1 | 1 | 1 | 1 | 0 | 0 | 1 | 0 | 1 | 1 | 1 | 1 | 1 | 1 | 1 | 0 | 1 | 1 | 1 | 1 | 518 |
| miR-483-5p\|0\|+1 | 1 | 1 | 0 | 1 | 1 | 1 | 1 | 1 | 1 | 1 | 0 | 0 | 1 | 1 | 1 | 0 | 0 | 0 | 0 | 1 | 0 | 0 | 1 | 1 | 1 | 1 | 1 | 1 | 0 | 0 | 1 | 581 |
| miR-514a-3p\|-2\|-1 | 0 | 0 | 1 | 1 | 0 | 1 | 1 | 1 | 1 | 1 | 1 | 1 | 1 | 1 | 1 | 0 | 1 | 1 | 0 | 1 | 1 | 1 | 1 | 1 | 1 | 0 | 0 | 1 | 1 | 1 | 1 | 591 |
| miR-508-3p\|+2\|0 | 0 | 0 | 1 | 1 | 0 | 0 | 1 | 0 | 1 | 1 | 0 | 0 | 1 | 1 | 1 | 0 | 0 | 1 | 0 | 1 | 1 | 1 | 1 | 1 | 1 | 1 | 0 | 1 | 1 | 1 | 1 | 1039 |
| miR-514a-3p\|-3\|-1 | 0 | 0 | 1 | 1 | 1 | 0 | 0 | 0 | 0 | 1 | 1 | 1 | 1 | 1 | 1 | 0 | 1 | 1 | 0 | 1 | 1 | 1 | 1 | 1 | 1 | 0 | 0 | 1 | 1 | 1 | 1 | 363 |
| miR-509-3p\|0\|0 | 0 | 0 | 1 | 1 | 1 | 0 | 1 | 0 | 1 | 1 | 0 | 0 | 1 | 1 | 1 | 0 | 0 | 1 | 0 | 1 | 1 | 1 | 1 | 1 | 1 | 1 | 0 | 1 | 1 | 1 | 1 | 1450 |
| miR-514a-3p\|0\|0 | 0 | 0 | 1 | 1 | 0 | 0 | 1 | 0 | 1 | 1 | 1 | 1 | 1 | 1 | 1 | 0 | 0 | 1 | 0 | 1 | 1 | 1 | 1 | 1 | 1 | 1 | 0 | 0 | 1 | 1 | 1 | 1084 |
| miR-10b-5p\|-1\|-1 | 0 | 1 | 1 | 1 | 1 | 0 | 1 | 1 | 1 | 1 | 0 | 0 | 1 | 0 | 1 | 0 | 0 | 0 | 1 | 0 | 1 | 1 | 1 | 1 | 0 | 1 | 1 | 0 | 1 | 0 | 1 | 1906 |
| miR-514a-3p\|-3\|0 | 0 | 1 | 1 | 0 | 1 | 1 | 1 | 0 | 0 | 1 | 1 | 1 | 1 | 1 | 1 | 0 | 0 | 0 | 0 | 1 | 0 | 1 | 1 | 1 | 1 | 1 | 1 | 1 | 1 | 0 | 1 | 280 |
| miR-514a-3p\|-2\|0 | 0 | 0 | 1 | 1 | 0 | 1 | 0 | 1 | 0 | 1 | 1 | 1 | 1 | 1 | 1 | 1 | 0 | 0 | 1 | 0 | 1 | 1 | 1 | 1 | 1 | 1 | 0 | 0 | 1 | 1 | 1 | 1521 |
| miR-483-5p\|0\|0 | 0 | 1 | 0 | 1 | 1 | 1 | 0 | 1 | 1 | 1 | 0 | 0 | 1 | 1 | 1 | 0 | 1 | 0 | 0 | 1 | 0 | 0 | 1 | 1 | 1 | 0 | 1 | 1 | 0 | 0 | 1 | 1011 |
| miR-483-5p\|+1\|+3 | 1 | 1 | 0 | 0 | 1 | 0 | 1 | 1 | 1 | 1 | 0 | 0 | 1 | 1 | 0 | 0 | 0 | 1 | 0 | 0 | 0 | 1 | 1 | 1 | 1 | 0 | 1 | 0 | 0 | 0 | 1 | 489 |
| miR-483-5p\|0\|-1 | 0 | 1 | 0 | 0 | 1 | 1 | 1 | 1 | 1 | 1 | 0 | 0 | 1 | 1 | 0 | 0 | 0 | 1 | 0 | 0 | 1 | 1 | 1 | 1 | 1 | 1 | 1 | 0 | 0 | 1 | 1 | 893 |
| miR-483-3p\|0\|+1 | 0 | 1 | 0 | 0 | 1 | 0 | 0 | 1 | 1 | 1 | 0 | 0 | 1 | 0 | 0 | 1 | 1 | 0 | 0 | 1 | 1 | 1 | 1 | 1 | 1 | 1 | 1 | 0 | 0 | 1 | 1 | 630 |

FIG. 7 cont.

| Row | Value |
|---|---|
| miR-483-3p\|+1\|+2 | 1143 |
| miR-508-3p\|0\|-3 | 504 |
| let-7e-5p\|0\|+2 | 1433 |
| miR-508-3p\|0\|-1 | 2210 |
| miR-508-3p\|0\|0 | 2720 |
| miR-542-3p\|-1\|0 | 2745 |
| miR-10b-3p\|0\|0 | 2878 |
| TJU_CMC_MD2.ID02736.5p-miR\|0\|0 | 3060 |
| miR-99b-3p\|0\|+1 | 2887 |
| miR-125a-5p\|0\|-4 | 2851 |
| let-7e-5p\|0\|-4 | 2220 |
| miR-503-5p\|0\|0 | 3407 |
| let-7e-5p\|0\|-4 | 2089 |
| miR-450a-5p\|0\|0 | 1969 |
| miR-10b-5p\|0\|-5 | 4517 |
| miR-328-3p\|0\|-1 | 3252 |
| miR-127-5p\|0\|+1 | 4260 |
| miR-542-3p\|-1\|-1 | 5015 |
| miR-1180-3p\|0\|0 | 5999 |
| miR-10b-5p\|+1\|-3 | 5677 |
| miR-1468-5p\|0\|+1 | 2960 |
| let-7f-5p\|0\|-3 | 6335 |
| miR-127-5p\|0\|0 | 7473 |
| miR-542-3p\|0\|+1 | 6079 |
| miR-450b-5p\|0\|-1 | 5206 |
| miR-181a-2-3p\|-1\|-1 | 4632 |
| miR-181b-5p\|0\|+2 | 3 |
| miR-766-3p\|0\|0 | 2524 |

FIG. 8

LEVERAGING THE PRESENCE OR ABSENCE OF MIRNA ISOFORMS FOR RECOMMENDING THERAPY IN CANCER PATIENTS

CROSS REFERENCE TO RELATED APPLICATIONS

This application claims priority to International Patent Application No. PCT/US2017/57909, filed Oct. 23, 2017, published on Apr. 26, 23018 as Publication No. WO 2018/076015, which claims priority to U.S. Provisional Patent Application No. 62/411,417, filed Oct. 21, 2016, U.S. Provisional Patent Application No. 62/441,837, filed Jan. 3, 2017, and U.S. Provisional Patent Application No. 62/502,133, filed May 5, 2017, each of which are hereby incorporated by reference in their entirety.

SEQUENCE LISTING

The instant application contains a Sequence Listing which has been filed electronically in ASCII format and is hereby incorporated by reference in its entirety. Said ASCII copy, created on Oct. 23, 2017, is named 6107-164PCT_SL.txt and is 1,261,782 bytes in size.

BACKGROUND OF INVENTION

In the post-genomic era, the flourishing of microarray and next-generation sequencing (NGS) technologies has made the generation of large amount of data a quick and relatively inexpensive process. As a result, the challenge nowadays is how to best manipulate and analyze big volumes of information. This has led to the development of novel tools, or the adaptation of previously-developed algorithms for use in the biological and medical fields (1).

During this time, the field of non-coding RNAs (ncRNAs) enjoyed very significant progress. In fact, RNA-sequencing technologies helped uncovered many novel categories of short and long RNA transcripts (2). In the process, they also revealed multiple layers of regulatory processes.

Among ncRNAs, microRNAs (miRNAs) are arguably the best-studied to date (3-5). The details of miRNA biogenesis (6-8) and function (7,9,10) were worked out more than a decade ago. Parallel studies linked miRNAs to a wide range of cellular, molecular and physiological processes in development (11-15), and homeostasis (16-18). In addition, miRNAs play important roles in physiological conditions and diseases (19-21), including cancer (22,23).

Their potent regulatory roles, small size, and relatively easy quantification have made miRNAs ideal targets as potential biomarkers (24-26). They also inspired research on their use as tumor classifiers. i.e. as features/variables used to construct statistical models to classify and/or predict the type of a given tumor. E.g., Lu et al. used hierarchical clustering to classify miRNA profiles of tumor samples into groups of cancer types (27). Subsequent work by Volinia et al. (28) and by Rosenfeld et al. (29) further demonstrated the power of the miRNA profile to classify tumors and predict cancer types.

More than two decades since their discovery, the mining of RNA-seq datasets continues to generate important observations about miRNAs. Perhaps most important is the ever-increasing repertoire of miRNAs, which has implications for the complexity of the miRNA regulatory layer. This was recently demonstrated by the discovery of numerous primate-specific miRNAs with tissue-dependent expression patterns (30). This complexity increased further with the recent discovery that miRNA isoforms (isomiRs) are constitutive, and their expression depends on sex, population, race, tissue type, tissue state, and disease subtype (31-34).

Several lines of evidence, both computational and experimental, support the functional importance of isomiRs. Intuitively, this is not surprising considering that isomiR profiles provide a richer and more granular representation of the molecules produced from each miRNA locus compared to the single molecule, the "archetype," that one finds listed in public databases. As we exemplified in the case of breast cancer, isomiRs are better in capturing breast cancer heterogeneity than the archetype miRNA (35). Recently, others and we also showed that distinct isomiRs originating from the same miRNA arm can target multiple distinct genes and molecular pathways (31,34,35).

The Cancer Genome Atlas (TCGA) initiative has been successfully integrating miRNA profiles with messenger RNA (mRNA) expression and genome-wide sequence information to further explain disease subtypes. More than 11,000 samples from more than two dozen cancer types have been profiled today at the levels of miRNA, mRNA, protein, epigenome, etc. Specifically for miRNAs and isomiRs, tools were developed to analyze TCGA's RNA-seq datasets and have generated what is a unique and rich resource for this kind of research (36).

SUMMARY OF INVENTION

Our recent analyses of expression profiles from hundreds of individuals showed that "how many" and "which" isomiRs are produced from a given miRNA locus depends on the locus and the tissue, among other variables (31, 35). This is in agreement with previous reports of miRNAs that are specifically expressed in some tissues but absent from other (30, 37). These findings suggest that miRNA expression signatures are complex and dynamic. They also support the notion of using miRNAs as biomarkers. An ideal miRNA-based biomarker should be specific to the cancer that it is used to diagnose and should not be present in other tissues or cancer types. This characteristic prompted us to investigate the usability of miRNAs and isomiRs as markers: they should be uniquely expressed (present) in the cancer under study and absent in all other cancers.

Here we describe our findings from a pan-cancer analysis of TCGA's short RNA-seq datasets. Specifically, we evaluated the ability of "binarized" expression profiles, or "binarized profiles" for short, (see below for a definition) that we built on isomiRs or the arms of miRNAs to discriminate among the 32 TCGA cancer types. For protein-coding transcripts, binarized profiles were shown previously to exhibit robustness to noise and to contain enough information to distinguish among tumor types (38, 39) and among tissues (40). A binarized profile can be thought of as a collection of features, each of which can assume one of two possible values. Typically, these values are 0 and 1. 0 indicates 'absence' of a feature whereas 1 indicates 'presence.' For isomiRs, we generated "binarized isomiR profiles" as follows: after thresholding in an adaptive manner, we ignored the isomiR's actual level of abundance and instead declared it present, if its expression exceeds threshold; otherwise, we declared it absent. We also evaluated the ability of "binarized miRNA-arm profiles" to discriminate among the 32 TCGA cancer types. In this case, we declared the 5p of the miRNA arm present, if at least one of its isomiRs is present above threshold, and absent otherwise. Analogously, we declared the 3p of the miRNA arm present, if at least one of its isomiRs is present above threshold, and absent otherwise. Recall that the typical miRNA precursor resembles a 'hairpin.' The hairpin arm that we encounter first when traversing the hairpin in the direction of transcription is referred to as the 'left' or 5p arm; the other arm is referred to as the 'right' or 3p arm. Clearly, the miRNA-arm representation greatly reduces the information that the analysis is allowed to use. The inventions described herein include a method of identifying a subject in need of therapeutic intervention to treat one or more of: adrenocortical carcinoma (ACC), bladder urothelial carcinoma (BLCA), breast invasive carcinoma (BRCA), cervical squamous cell carcinoma and endocervical adenocarcinoma (CESC), cholangiocarcinoma (CHOL), colon adenocarcinoma (COAD), lymphoid neoplasm diffuse large B-cell lymphoma (DLBC), esophageal carcinoma (ESCA), head and neck squamous cell carcinoma (HNSC), kidney chromophobe (KICH), kidney renal clear cell carcinoma (KIRC), kidney renal papillary cell carcinoma (KIRP), acute myeloid leukemia (LAML), brain lower grade glioma (LGG), liver hepatocellular carcinoma (LIHC), lung adenocarcinoma (LUAD), lung squamous cell carcinoma (LUSC), mesothelioma (MESO), ovarian serous cystadenocarcinoma (OV), pancreatic adenocarcinoma (PAAD), pheochromocytoma and paraganglioma (PCPG), prostate adenocarcinoma (PRAD), rectum adenocarcinoma (READ), sarcoma (SARC), skin cutaneous melanoma (SKCM), stomach adenocarcinoma (STAD), testicular germ cell tumors (TGCT), thyroid carcinoma (THCA), thymoma (THYM), uterine corpus endometrial carcinoma (UCEC), uterine carcinosarcoma (UCS), uveal melanoma (UVM), or, progression of one or more of ACC, BLCA, BRCA, CESC, CHOL, COAD, DLBC, ESCA, HNSC, KICH, KIRC, KIRP, LAML, LGG, LIHC, LUAD, LUSC, MESO, OV, PAAD, PCPG, PRAD, READ, SARC, SKCM, STAD, TGCT, THCA, THYM, UCEC, UCS, UVM or, recurrence of one or more of ACC, BLCA, BRCA, CESC, CHOL, COAD, DLBC, ESCA, HNSC, KICH, KIRC, KIRP, LAML, LGG, LIHC, LUAD, LUSC, MESO, OV, PAAD, PCPG, PRAD, READ, SARC, SKCM, STAD, TGCT, THCA, THYM, UCEC, UCS, UVM comprising, isolating miRNAs from a sample obtained from the subject; and characterizing the presence or absence in the sample of either the isomiRs or of the arms of the miRNA precursors to identify a signature, wherein when the signature is indicative of a diagnosis of the disease then treatment of the subject is recommended.

In preferred embodiments, the sample is isolated from one or more cells, tissue or body fluid obtained from the subject. Preferentially, when the sample is a body fluid, it is selected from the group consisting of amniotic fluid, aqueous humour and vitreous humour, bile, blood serum, breast milk, cerebrospinal fluid, cerumen, chyle, chyme, endolymph and perilymph, exudates, feces, female ejaculate, gastric acid, gastric juice, lymph, mucus, pericardial fluid, peritoneal fluid, pleural fluid, pus, rheum, saliva, sebum, serous fluid, semen, smegma, sputum, synovial fluid, sweat, tears, urine, vaginal secretion, and vomit.

By contrast, a sample can also be selected from the group consisting of one or more peripheral blood cells, one or more tumor cells, a one or more circulating tumor cells, or a one or more exosomes.

When performing the method as described above, the miRNAs or isomiRs are isolated by a method selected from the group consisting of size selection, sequencing, and amplification. Preferably the miRNAs or isomiRs with a length in the range of about 15 nucleotides to about 25 nucleotides are isolated.

In certain embodiments, the signature is obtained through deep sequencing, or the signature is obtained by hybridization to a panel of oligonucleotides, or the signature is obtained through a quantification method that is specific to the termini of the sought molecule (or molecules).

Certain embodiments allow the method as described above, wherein the actual abundance of the isolated miRNAs is not taken into account by subsequent analyses.

A further embodiment is directed to a method of identifying a subject in need of therapeutic intervention to treat one or more of ACC, BLCA, BRCA, CESC, CHOL, COAD, DLBC, ESCA, HNSC, KICH, KIRC, KIRP, LAML, LGG, LIHC, LUAD, LUSC, MESO, OV, PAAD, PCPG, PRAD, READ, SARC, SKCM, STAD, TGCT, THCA, THYM, UCEC, UCS, UVM or, progression of one or more of ACC, BLCA, BRCA, CESC, CHOL, COAD, DLBC, ESCA, HNSC, KICH, KIRC, KIRP, LAML, LGG, LIHC, LUAD, LUSC, MESO, OV, PAAD, PCPG, PRAD, READ, SARC, SKCM, STAD, TGCT, THCA, THYM, UCEC, UCS, UVM, or recurrence of one or more of ACC, BLCA, BRCA, CESC, CHOL, COAD, DLBC, ESCA, HNSC, KICH, KIRC, KIRP, LAML, LGG, LIHC, LUAD, LUSC, MESO, OV, PAAD, PCPG, PRAD, READ, SARC, SKCM, STAD, TGCT, THCA, THYM, UCEC, UCS, UVM: a classifier that has been trained using as positive examples samples from one or more of ACC, BLCA, BRCA, CESC, CHOL, COAD, DLBC, ESCA, HNSC, KICH, KIRC, KIRP, LAML, LGG, LIHC, LUAD, LUSC, MESO, OV, PAAD, PCPG, PRAD, READ, SARC, SKCM, STAD, TGCT, THCA, THYM, UCEC, UCS, UVM, and as negative examples disease-free samples or samples from non-cancer diseases or samples from cancers other than ACC, BLCA, BRCA, CESC, CHOL, COAD, DLBC, ESCA, HNSC, KICH, KIRC, KIRP, LAML, LGG, LIHC, LUAD, LUSC, MESO, OV, PAAD, PCPG, PRAD, READ, SARC, SKCM, STAD, TGCT, THCA, THYM, UCEC, UCS, UVM wherein said classifier uses features that are based on knowledge of the presence or absence of expression of one or more isomiRs of interest or of one or both arms of one or more miRNA precursors of interest; focusing on isomiRs or on miRNAs from a sample obtained from the subject; characterizing the presence or absence of expression of one or more isomiRs of interest or of one or both arms of one or more miRNA precursors of interest in the sample to identify a signature for the sample; using the classifier to evaluate the signature of the sample; and, recommending treatment of the subject if the signature of the sample is indicative of a diagnosis of the disease. Negative examples can include samples from ACC, BLCA, BRCA, CESC, CHOL, COAD, DLBC, ESCA, HNSC, KICH, KIRC, KIRP, LAML, LGG, LIHC, LUAD, LUSC, MESO, OV, PAAD, PCPG, PRAD, READ, SARC, SKCM, STAD, TGCT, THCA, THYM, UCEC, UCS, UVM as long as samples from a given cancer type are not simultaneously given as positive and negative examples to a classifier aimed at distinguishing among cancer types. Negative examples can include samples from ACC, BLCA, BRCA, CESC, CHOL, COAD, DLBC, ESCA, HNSC, KICH, KIRC, KIRP, LAML, LGG, LIHC, LUAD, LUSC, MESO, OV, PAAD, PCPG, PRAD, READ, SARC, SKCM, STAD, TGCT, THCA, THYM, UCEC, UCS, UVM as long as samples from a given cancer sub-type are not simultaneously given as positive and negative examples to a classifier aimed at distinguishing among cancer sub-types.

Preferably, the sample is isolated from one or more cells, from tissue, or from body fluid obtained from the subject. In certain embodiments, the body fluid is selected from the group consisting of amniotic fluid, aqueous humour and vitreous humour, bile, blood serum, breast milk, cerebrospinal fluid, cerumen, chyle, chyme, endolymph and perilymph, exudates, feces, female ejaculate, gastric acid, gastric juice, lymph, mucus, pericardial fluid, peritoneal fluid, pleural fluid, pus, rheum, saliva, sebum, serous fluid, semen, smegma, sputum, synovial fluid, sweat, tears, urine, vaginal secretion, and vomit. In other embodiments, the sample is selected from the group consisting of one or more peripheral blood cells, one or more tumor cells, one or more circulating tumor cells, or one or more exosome.

In certain methods, the selection of isomiRs or miRNAs is through a method selected from the group consisting of size selection, sequencing, and amplification. For example, the method where isomiRs or miRNAs with a length in the range of about 15 nucleotides to about 25 nucleotides are isolated.

In certain embodiments, a method may derive or acquire the signature through deep sequencing, or by hybridization to a panel of oligonucleotides, or through use of one or more qRT-PCR assays, or of related variants. For example, a method may derive or acquire the signature through a quantification method that is specific to the termini of the sought molecule (or molecules).

In certain embodiments, the actual abundance of the miRNAs is not considered by subsequent analyses. In other embodiments, only the presence or absence of the miRNAs is considered by subsequent analyses. In other embodiments, an arm of a miRNA precursor is considered present if at least one of the distinct molecules that the arm could produce is present, or wherein an arm of a miRNA precursor is considered absent if none of the distinct molecules that the arm could produce is present.

In the embodiments, a suitable step further comprises administration of a suitable therapeutic for treatment of the disease.

In certain embodiments, the positive examples include only samples from one of ACC, BLCA, BRCA, CESC, CHOL, COAD, DLBC, ESCA, HNSC, KICH, KIRC, KIRP, LAML, LGG, LIHC, LUAD, LUSC, MESO, OV, PAAD, PCPG, PRAD, READ, SARC, SKCM, STAD, TGCT, THCA, THYM, UCEC, UCS, UVM. In other embodiments, the positive examples included samples from at least two of ACC, BLCA, BRCA, CESC, CHOL, COAD, DLBC, ESCA, HNSC, KICH, KIRC, KIRP, LAML, LGG, LIHC, LUAD, LUSC, MESO, OV, PAAD, PCPG, PRAD, READ, SARC, SKCM, STAD, TGCT, THCA, THYM, UCEC, UCS, UVM.

In a preferred embodiment, a method for identifying a subject in need of therapeutic intervention to treat one or more of ACC, BLCA, BRCA, CESC, CHOL, COAD, DLBC, ESCA, HNSC, KICH, KIRC, KIRP, LAML, LGG, LIHC, LUAD, LUSC, MESO, OV, PAAD, PCPG, PRAD, READ, SARC, SKCM, STAD, TGCT, THCA, THYM, UCEC, UCS, UVM, or identifying progression of one or more of ACC, BLCA, BRCA, CESC, CHOL, COAD, DLBC, ESCA, HNSC, KICH, KIRC, KIRP, LAML, LGG, LIHC, LUAD, LUSC, MESO, OV, PAAD, PCPG, PRAD, READ, SARC, SKCM, STAD, TGCT, THCA, THYM, UCEC, UCS, UVM, or identifying recurrence of one or more of ACC, BLCA, BRCA, CESC, CHOL, COAD, DLBC, ESCA, HNSC, KICH, KIRC, KIRP, LAML, LGG, LIHC, LUAD, LUSC, MESO, OV, PAAD, PCPG, PRAD, READ, SARC, SKCM, STAD, TGCT, THCA, THYM, UCEC, UCS, UVM may utilize a classifier that has been trained using as features at least 7,466 isomiRs, or a classifier that has been trained using as features at least 2,588 isomiRs, or a classifier that has been trained using as features at least 1,883 isomiRs, or a classifier that has been trained using as features at least 1,147 isomiRs, or a classifier that has been trained using as features at least 456 isomiRs, or a classifier that has been trained using as features at least 172 isomiRs.

In a preferred embodiment, the 7,466 isomiRs include one or more of the sequences with identifiers SEQ ID NO: 1 through SEQ ID NO:7,466 inclusive.

In a preferred embodiment, the 2,588 isomiRs include one or more of the sequences with identifiers SEQ ID NO: 1 through SEQ ID NO: 2,588 inclusive.

In a preferred embodiment, the 1,883 isomiRs include one or more of the sequences with identifiers SEQ ID NO: 1 through SEQ ID NO: 1,883 inclusive.

In a preferred embodiment, the 1,147 isomiRs include one or more of the sequences with identifiers SEQ ID NO: 1 through SEQ ID NO: 1,147 inclusive.

In a preferred embodiment, the 456 isomiRs include one or more of the sequences with identifiers SEQ ID NO: 1 through SEQ ID NO: 456 inclusive.

These embodiments preferably provide a method, wherein the average sensitivity can be as high as 90% and wherein the average false detection rate can be less than 3%.

The methods for identifying a subject in need of therapeutic intervention to treat one or more of ACC, BLCA, BRCA, CESC, CHOL, COAD, DLBC, ESCA, HNSC, KICH, KIRC, KIRP, LAML, LGG, LIHC, LUAD, LUSC, MESO, OV, PAAD, PCPG, PRAD, READ, SARC, SKCM, STAD, TGCT, THCA, THYM, UCEC, UCS, UVM, or identifying progression of one or more of ACC, BLCA, BRCA, CESC, CHOL, COAD, DLBC, ESCA, HNSC, KICH, KIRC, KIRP, LAML, LGG, LIHC, LUAD, LUSC, MESO, OV, PAAD, PCPG, PRAD, READ, SARC, SKCM, STAR, TGCT, THCA, THYM, UCEC, UCS, UVM, or identifying recurrence of one or more of ACC, BLCA, BRCA, CESC, CHOL, COAD, DLBC, ESCA, HNSC, KICH, KIRC, KIRP, LAML, LGG, LIHC, LUAD, LUSC, MESO, OV, PAAD, PCPG, PRAD, READ, SARC, SKCM, STAD, TGCT, THCA, THYM, UCEC, UCS, UVM may advantageously employ a classifier that has been trained using as features at least 456 isomiRs, or at least 1,147 isomiRs, or at least 1,883 isomiRs, or at least 2,588 isomiRs, or at least 7,466 isomiRs.

The methods for identifying a subject in need of therapeutic intervention to treat one or more of ACC, BLCA, BRCA, CESC, CHOL, COAD, DLBC, ESCA, HNSC, KICH, KIRC, KIRP, LAML, LGG, LIHC, LUAD, LUSC, MESO, OV, PAAD, PCPG, PRAD, READ, SARC, SKCM, STAR, TGCT, THCA, THYM, UCEC, UCS, UVM, or identifying progression of one or more of ACC, BLCA, BRCA, CESC, CHOL, COAD, DLBC, ESCA, HNSC, KICH, KIRC, KIRP, LAML, LGG, LIHC, LUAD, LUSC, MESO, OV, PAAD, PCPG, PRAD, READ, SARC, SKCM, STAR, TGCT, THCA, THYM, UCEC, UCS, UVM, or identifying recurrence of one or more of ACC, BLCA, BRCA, CESC, CHOL, COAD, DLBC, ESCA, HNSC, KICH, KIRC, KIRP, LAML, LGG, LIHC, LUAD, LUSC, MESO, OV, PAAD, PCPG, PRAD, READ, SARC, SKCM, STAR, TGCT, THCA, THYM, UCEC, UCS, UVM may advantageously utilize a classifier that has been trained using as features at least 807 arms of miRNA precursors, or a classifier that has been trained using as features at least 285 arms of miRNA precursors, or a classifier that has been trained using as features at least 198 arms of miRNA precursors, or a classifier that has been trained using as features at least 115 arms of miRNA precursors, or a classifier that has been trained using at least 47 arms of miRNA precursors, or a classifier that has been trained using at least 21 arms of miRNA precursors.

In a preferred embodiment, the 807 arms of miRNA precursors include one or more of the sequences with identifiers SEQ ID NO: 7,467 through SEQ ID NO: 8,273 inclusive.

In a preferred embodiment, the 285 arms of miRNA precursors include one or more of the sequences with identifiers SEQ ID NO: 7,467 through SEQ ID NO: 7,751 inclusive.

In a preferred embodiment, the 198 arms of miRNA precursors include one or more of the sequences with identifiers SEQ ID NO: 7,467 through SEQ ID NO: 7,664 inclusive.

In a preferred embodiment, the 115 arms of miRNA precursors include one or more of the sequences with identifiers SEQ ID NO: 7,467 through SEQ ID NO: 7,581 inclusive.

In a preferred embodiment, the 47 arms of miRNA precursors include one or more of the sequences with identifiers SEQ ID NO: 7,467 through SEQ ID NO: 7,513 inclusive.

These embodiments preferably provide a method, wherein the average sensitivity can be as high as 83% and wherein the average false detection rate can be less than 6%.

The methods for identifying a subject in need of therapeutic intervention to treat one or more of ACC, BLCA, BRCA, CESC, CHOL, COAD, DLBC, ESCA, HNSC, KICH, KIRP, LAML, LGG, LIHC, LUAD, LUSC, MESO, OV, PAAD, PCPG, PRAD, READ, SARC, SKCM, STAD, TGCT, THCA, THYM, UCEC, UCS, UVM, or identifying progression of one or more of ACC, BLCA, BRCA, CESC, CHOL, COAD, DLBC, ESCA, HNSC, KICH, KIRC, KIRP, LAML, LGG, LIHC, LUAD, LUSC, MESO, OV, PAAD, PCPG, PRAD, READ, SARC, SKCM, STAD, TGCT, THCA, THYM, UCEC, UCS, UVM, or identifying recurrence of one or more of ACC, BLCA, BRCA, CESC, CHOL, COAD, DLBC, ESCA, HNSC, KICH, KIRC, KIRP, LAML, LGG, LIHC, LUAD, LUSC, MESO, OV, PAAD, PCPG, PRAD, READ, SARC, SKCM, STAD, TGCT, THCA, THYM, UCEC, UCS, UVM may advantageously employ a classifier that has been trained using as features at least 47 arms of miRNA precursors, or at least 115 arms of miRNA precursors, or at least 198 arms of miRNA precursors, or at least 285 arms of miRNA precursors, or at least 807 arms of miRNA precursors.

The methods for identifying a subject in need of therapeutic intervention to treat STAD, or identifying progression of STAD, or identifying recurrence of STAD may utilize a classifier that has been trained using as features at least 161 arms of miRNA precursors, or a classifier that has been trained using as features at least 80 arms of miRNA precursors, or a classifier that has been trained using as features at least 40 arms of miRNA precursors, or a classifier that has been trained using as features at least 24 arms of miRNA precursors, or a classifier that has been trained using as features at least 16 arms of miRNA precursors.

In a preferred embodiment, the 161 arms of miRNA precursors include one or more of the sequences with identifiers SEQ ID NO: 8,274 through SEQ ID NO: 8,434 inclusive.

In a preferred embodiment, the 80 arms of miRNA precursors include one or more of the sequences with identifiers SEQ ID NO: 8,274 through SEQ ID NO: 8,353 inclusive.

In a preferred embodiment, the 40 arms of miRNA precursors include one or more of the sequences with identifiers SEQ ID NO: 8,274 through SEQ ID NO: 8,313 inclusive.

In a preferred embodiment, the 24 arms of miRNA precursors include one or more of the sequences with identifiers SEQ ID NO: 8,274 through SEQ ID NO: 8,297 inclusive.

In a preferred embodiment, the 16 arms of miRNA precursors include one or more of the sequences with identifiers SEQ ID NO: 8,274 through SEQ ID NO: 8,289 inclusive.

These embodiments preferably provide a method, wherein the average sensitivity can be as high as 69% and wherein the average false detection rate can be less than 18%.

The methods for identifying a subject in need of therapeutic intervention to treat STAD, or identifying progression of STAD, or identifying recurrence of STAD may advantageously employ a classifier that has been trained using as features at least 16 arms of miRNA precursors, or at least 24 arms of miRNA precursors, or at least 40 arms of miRNA precursors, or at least 80 arms of miRNA precursors, or at least 161 arms of miRNA precursors.

The methods for identifying a subject in need of therapeutic intervention to treat one or more of STAD, COAD, READ, ESCA, PAAD, or identifying progression of one or more of STAD, COAD, READ, ESCA, PAAD, or identifying recurrence of one or more of STAD, COAD, READ, ESCA, PAAD may utilize a classifier that has been trained using as features at least 161 arms of miRNA precursors, or a classifier that has been trained using as features at least 80 arms of miRNA precursors, or a classifier that has been trained using as features at least 40 arms of miRNA precursors, or a classifier that has been trained using as features at least 24 arms of miRNA precursors, or a classifier that has been trained using as features at least 16 arms of miRNA precursors.

For example, the 161 arms of miRNA precursors include one or more of the sequences with identifiers SEQ ID NO: 8,435 through SEQ ID NO: 8,595 inclusive.

In a preferred embodiment, the 80 arms of miRNA precursors include one or more of the sequences with identifiers SEQ ID NO: 8,435 through SEQ ID NO: 8,514 inclusive.

In a preferred embodiment, the 40 arms of miRNA precursors include one or more of the sequences with identifiers SEQ ID NO: 8,435 through SEQ ID NO: 8,474 inclusive.

In a preferred embodiment, the 24 arms of miRNA precursors include one or more of the sequences with identifiers SEQ ID NO: 8,435 through SEQ ID NO: 8,458 inclusive.

In a preferred embodiment, the 16 arms of miRNA precursors include one or more of the sequences with identifiers SEQ ID NO: 8,435 through SEQ ID NO: 8,450 inclusive.

These embodiments preferably provide a method, wherein the average sensitivity can be as high as 93% and wherein the average false detection rate can be less than 5%.

A further embodiment is directed to a method of identifying a subject in need of therapeutic intervention to treat one or more of ACC, BLCA, BRCA, CESC, CHOL, COAD, DLBC, ESCA, HNSC, KICH, KIRC, KIRP, LAML, LGG, LIHC, LUAD, LUSC, MESO, OV, PAAD, PCPG, PRAD, READ, SARC, SKCM, STAD, TGCT, THCA, THYM, UCEC, UCS, UVM, or identifying progression of one or more of ACC, BLCA, BRCA, CESC, CHOL, COAD, DLBC, ESCA, HNSC, KICH, KIRC, KIRP, LAML, LGG, LIHC, LUAD, LUSC, MESO, OV, PAAD, PCPG, PRAD, READ, SARC, SKCM, STAD, TGCT, THCA, THYM, UCEC, UCS, UVM, or identifying recurrence of one or more of ACC, BLCA, BRCA, CESC, CHOL, COAD, DLBC, ESCA, HNSC, KICH, KIRC, KIRP, LAML, LGG, LIHC, LUAD, LUSC, MESO, OV, PAAD, PCPG, PRAD, READ, SARC, SKCM, STAD, TGCT, THCA, THYM, UCEC, UCS, UVM; comprising, isolating isomiRs or isolating miRNAs from a sample obtained from the subject; and characterizing the isomiRs or the arms of miRNA precursors and their presence or absence in the sample to identify a signature, wherein when the signature is indicative of a diagnosis of the disease then treatment of the subject is recommended.

A method of identifying a subject in need of therapeutic intervention to treat a disease or condition or disease recurrence or disease progression comprising, isolating isomiRs or miRNAs from a sample obtained from the subject; and characterizing the isomiRs or miRNAs and their presence or absence in the sample to identify a signature, wherein when the signature is indicative of a diagnosis of the disease then treatment of the subject is recommended.

A method of treating a subject in need of therapeutic intervention to treat a disease or condition or disease recurrence or disease progression comprising, isolating isomiRs or miRNAs from a sample obtained from the subject; characterizing the isomiRs or miRNAs and their presence or absence in the sample to identify a signature, wherein the characterization of the isomiRs or miRNAs is selected from sequences SEQ ID NO: 1 through SEQ ID NO:7,466, or SEQ ID NO: 7,467 through SEQ ID NO: 8,273; wherein when the signature is indicative of a diagnosis of a disease; treating said subject with a therapeutic corresponding to the disease.

Any of the above embodiments may be combined in whole or part with one another, as appropriate and understood by those of ordinary skill in the art.

BRIEF DESCRIPTION OF THE DRAWINGS

FIG. 7 illustrates differentially present isomiRs among cancers. Shown is a partial such list for one cancer (ACC). The full list of tables is provided in Application No. 62/411,417. In the shown list, a positive (+1) value indicates that the isomiR is present in ACC (see title above the table) and absent in the cancer shown in the header of the respective column. A negative (−1) value indicates the opposite. A value of '0' indicates no differential presence between ACC and the cancer shown in the header of the respective column.

Figure 8:
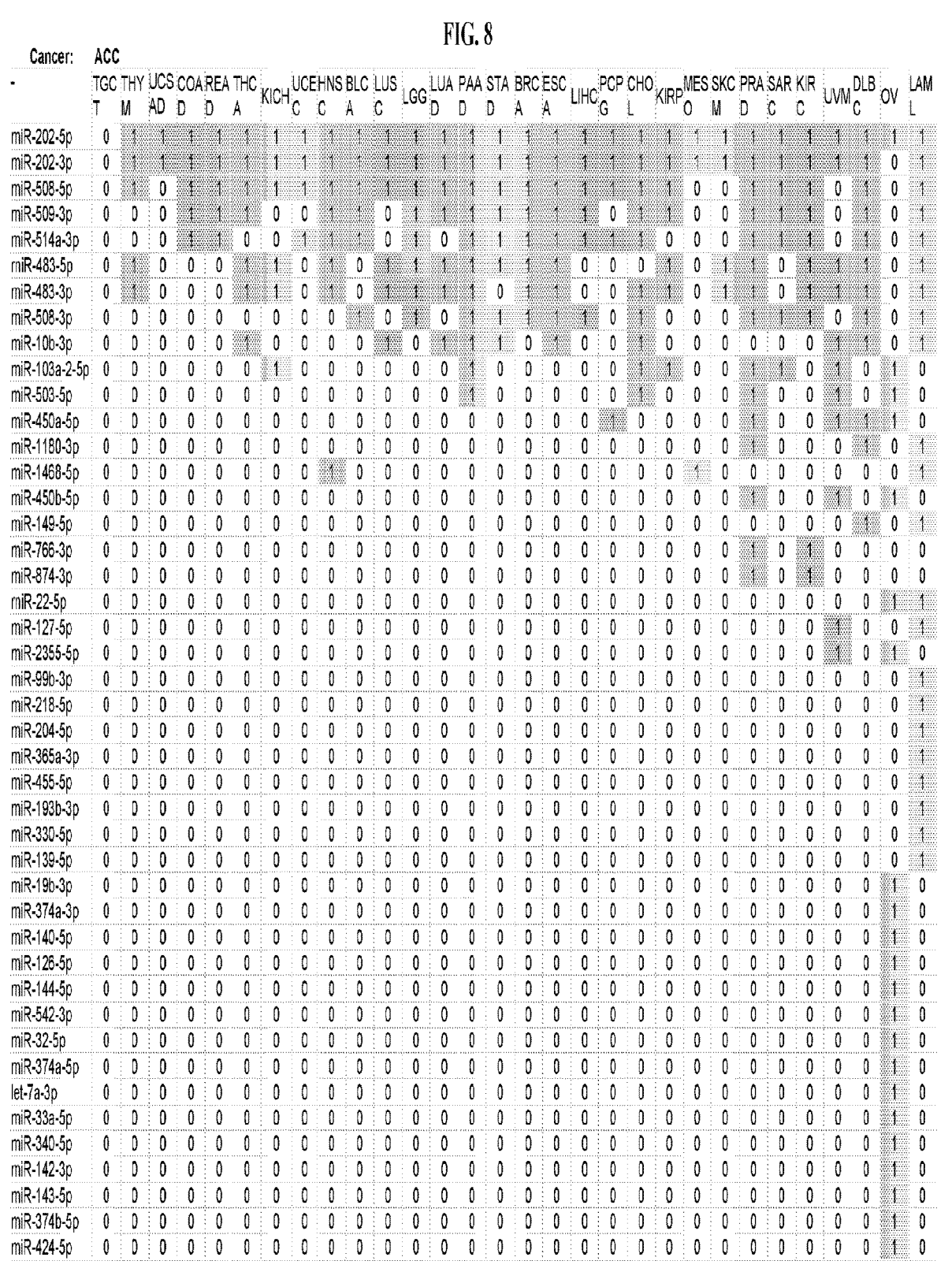

FIG. 8 illustrates differentially present miRNA arms among cancers. Shown is a partial such list for one cancer (ACC). The full list of tables is provided in Application No. 62/411,417. In the shown list, a positive (+1) value indicates that the miRNA arm is present in ACC (see title above the table) and absent in the cancer shown in the header of the respective column. A negative (−1) value indicates the opposite. A value of '0' indicates no differential presence between ACC and the cancer shown in the header of the respective column.

DETAILED DESCRIPTION OF THE EMBODIMENTS

Materials and Methods

Data Acquisition and Correction

Figure 1A:
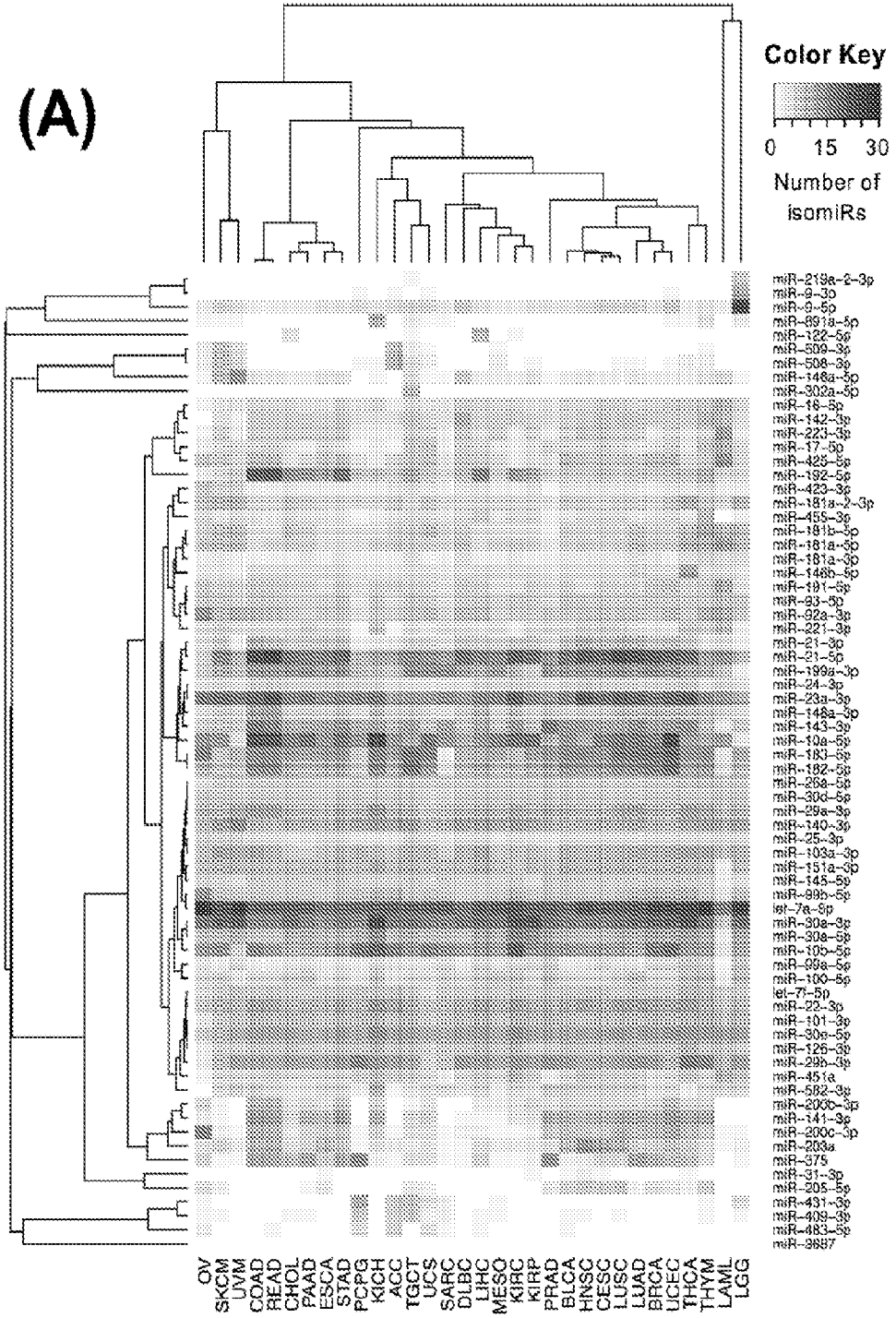
FIGS. 1A-1D illustrate differentially present isomiRs among different cancer types. (A) Heatmap of the number of isomiRs per miRNA arm. The darker the color of each cell, the higher the number of isomiRs that the respective arm (rows of the heatmap) produces in the respective cancer type (columns of the heatmap). (B) Differential presence of isomiRs in lower grade glioma (LGG) tumor samples as compared to the rest of cancer types. Dark gray indicates that the isomiR (row) was found as 'present' in LGG as compared to the respective cancer type (column), while light gray indicates 'absence' in LGG. The data for all possible pairwise comparisons are included in Application No. 62/411,417. (C) Overlap between miRNA arms and isomiRs in the comparison of colon adenocarcinoma (COAD) with the rest of the cancer types. Dark gray indicates that both the isomiR and the arm were 'present' in COAD as compared to at least one other cancer type, light gray indicates they were 'absent'. For example, miR-205-5p was 'absent' in COAD as well as its five isomiRs, miR-205-5p|0|0, miR-205-5p|0|-3, miR-205-5p|0|-2, miR-205-5p|0|-1 and miR-205-5p|0|+1. (D) Hierarchical clustering (complete method) considering the number of differentially present isomiRs as the distance between cancer types.

We quantified the TCGA isomiR expression data of 10,271 samples at the molecule/isomiR-sequence level. In order to do this, we took the publicly downloadable loci-based isoform.quantification.txt files from the TCGA datasets (downloaded from the TCGA data portal https://tcga-data.nci.nih.gov on Aug. 6, 2015) and converted them to be molecule/sequence based. We corrected for (a) the observation that if a mature sequence could come from multiple loci, loci-based expression assignment was arbitrarily, (b) the fact that the isoform.quantification.txt files often included only a subset of possible loci for ambiguously transcribed miRNA loci and (c) including our previously reported novel miRNAs (30) to the isomiR expression files if they came from one of the mapped hairpins. Importantly, while we looked at expression level at the molecule level, we still recorded all possible loci from which an isomiR may have been transcribed.

For our analyses, we used all TCGA samples from 32 cancer types. We excluded from our analyses all samples that were specifically annotated (file_annotations.txt files of the Clinical Data from the TCGA data portal, downloaded on 28 Oct. 2015), resulting in 9,745 samples. We further filtered non-tumor samples, e.g. normal adjacent tissue or metastastic samples, including only samples that had a sample infix of '01' or '03' in the TCGA barcode name.

Binarized IsomiR and miRNA Arm Profiles

We worked on a per-sample basis in order to generate the binarized isomiR profiles. Specifically, for each sample independently we considered the top 20% most expressed isomiRs as 'present'. As we described above, to generate the binarized miRNA arm profiles, we collapsed the information at the arm level: if there was at least one isomiR (originating from the respective arm) that was characterized as 'present', then the arm was also marked as 'present'. There are cases where an isomiR could be mapped exactly to more than one miRNA arms. In such instances, we merged all the miRNA arms that shared an isomiR into "meta-arms." There are several dozen meta-arms that arise in our analyses. We discuss this again below.

Statistical and Machine Learning Analyses

Analyses were done in R and python. Specifically, hamming distance was calculated with the hamming distance function of the e1071 package, while all other distance metrics of hierarchical clustering (HCL) were performed with the cluster function of the amap package. Visualization of dendrograms was performed with the dendextend package of R. $X^2$ tests were performed and P values were corrected to FDR values. Significance in the $x^2$ test was further filtered so that the absolute difference between the percentage (%) of samples containing the isomiR or miRNA arm in one cancer but not the other had to be greater than or equal to 80%. Networks were visualized using the igraph package in R SVMs were run with the svm function of the e1071 package in R with linear kernel function and with allowed probability predictions. After the SVM model was trained, the probability vectors (one per sample) were computed for each sample in the test set. Each vector has 32 elements each one representing the probability that the given sample is of the respective cancer type. The sample is classified to the cancer type with the highest probability unless this probability is lower than 0.5. In this case, we classify the sample in the 'Other' category. Sensitivity and FDR scores were estimated per cancer per iteration. Sensitivity was defined as the number of true positive classifications divided by the total number of samples, while FDR was calculated as the number of false positive samples divided by the number of samples identified as cancer, i.e. non-Other. The VI scores were computed per isomiR or miRNA arm as the average of the square values of the weights across all pairwise SVM comparisons and then were scaled to 1 by dividing by the maximum score. RandomForest was run with the H2O package in R.

PubMed entries were found per miRNA gene. The unique gene identifiers in the Gene database of NCBI were retrieved and the number of links to PubMed entries was counted (as of Oct. 7, 2016).

Results

Preliminary Material and Definition

We analyzed the isomiR expression profiles for 10,271 samples from 32 cancer types. To deal with miRNAs with multiple genomic copies (paralogues), we worked at the level of the sequenced reads: thusly, for isomiRs whose sequences exist at more than one genomic locus we kept one representative instance avoiding multiple counting. Consequently, we represented each sample using an expression vector with as many dimensions as the number of distinct isomiR sequences that are expressed in the sample.

Figure 6:
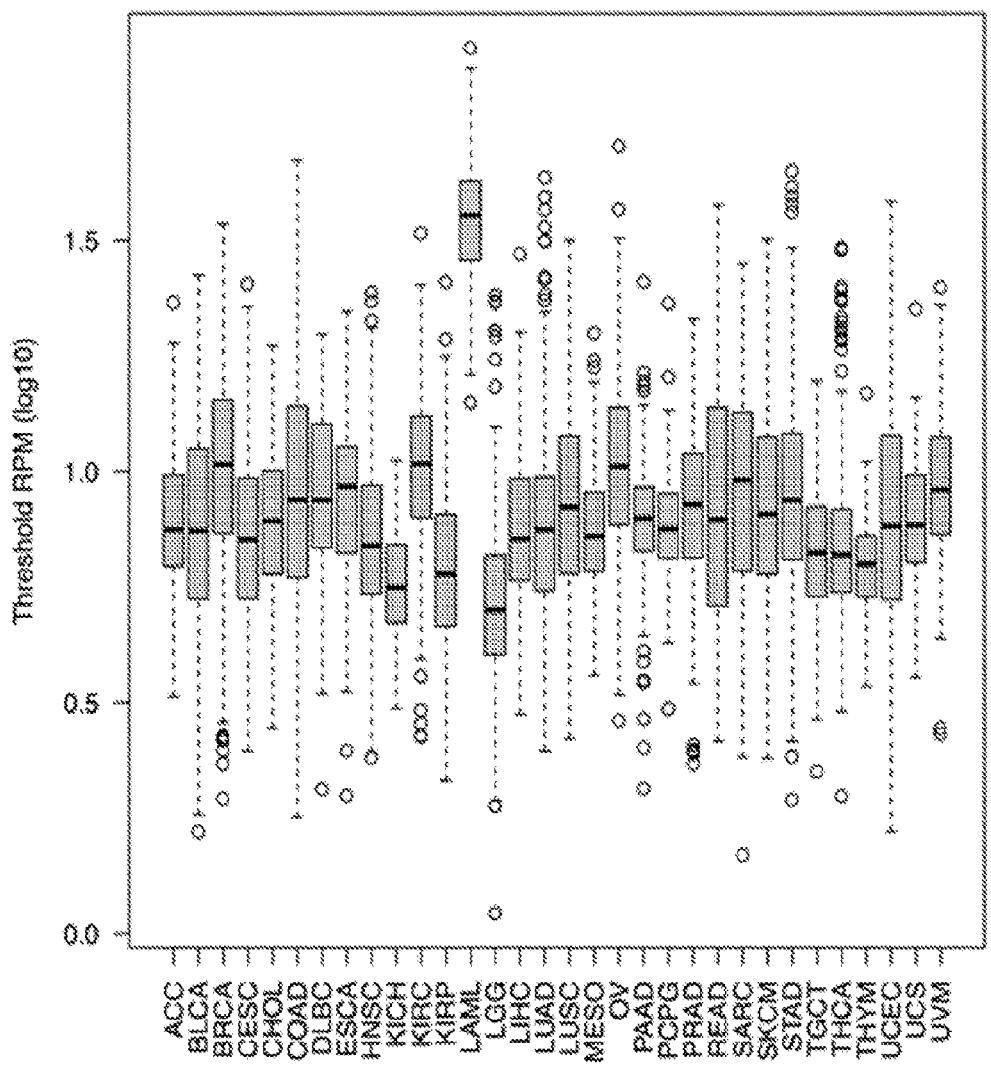
FIG. 6 illustrates the quantization threshold per sample per cancer type. The mean threshold for all samples included in our study was 9.7 RPM.

As mentioned already, we intentionally focus on binarized isomiR profiles, i.e. profiles that simply list an isomiR as present or absent. We determined an isomiR's presence or absence independently for each sample and without any influences by the isomiR's genomic origin. Binarization of isomiR abundances proceeded as follows: within the sample at hand, we considered as "present" the top 20% most abundant isomiRs; all other isomiRs were labeled "absent." In the case of the TCGA datasets, drawing the line at the top 20%, represented an average threshold of ~10 reads per million (RPM), i.e. 10 RPM, which is a stringent threshold (FIG. 6).

In addition to working with the binarized profiles of isomiRs, we also explored an alternative scheme, namely "miRNA-arm binarization." This representation scheme collapses the information captured by multiple isomiRs into a single statement of "present" or "absent." As already stated, if a miRNA arm, either 5p or 3p, has at least one of its isomiRs labeled "present," then this arm is labeled as "present," otherwise it is labeled "absent."

Statistics of Binarized IsomiRs

By processing the 10,271 TCGA samples, we accumulated a total of 7,466 isomiRs that passed threshold in at least one sample. These isomiRs arise from 807 arms that correspond to 515 known miRNA genes and 40 miRNA genes among the newly discovered miRNAs that were reported by Londin et al. (30). As provided in Application No. 62/411,417, Supp. Tables S1 and S2 list the binarized expression profiles for isomiRs and miRNA arms, respectively. Such data is incorporated by reference in its entirety. Our analyses were carried out on the samples corresponding to primary solid tumors (sample infix '01' in the TCGA sample barcode) except for LAML where blood-derived samples were used (sample infix '03'), including a total of 9,291 datasets (tumor samples) and 7,271 isomiRs.

By analyzing the 7,271 isomiRs that occupy the 20% most abundant positions in at least one sample, we found that the vast majority of them (90.2%) are present in fewer than half of the analyzed tumor samples. Only 48 out of the 7,271 isomiRs are present in all datasets. Interestingly, 11 of the 48 isomiRs arise from loci that belong to the let-7 family of miRNAs. Other isomiRs that are present in many of the analyzed datasets arise from widely-studied miRNA loci including miR-21, miR-29, miR-30, the miR-17/92 cluster and its paralogues. For individual miRNA loci, the distribution of their isomiRs varied greatly across samples. For example, let-7 isomiRs were "dichotomized:" one subset is present in most of the TCGA datasets whereas a second subset is present in fewer than 25% of the datasets.

A significant portion (58.8%) of the 7,271 isomiRs is present in fewer than 100 samples each. Moreover, 77.5% of the 7,271 isomiRs are present in at least two of the 32 distinct cancer types. These findings suggest that the expression of many of the identified isomiRs has a cancer-specific dimension.

FIG. 1A depicts as a heatmap the variation in the number of isomiRs from a given locus. Only the top 70 loci from the standpoint of the isomiRs they produce are shown in the heatmap. As can be seen let-7a-5p consistently produces numerous isomiRs independent of cancer type. MiR-21-5p and miR-30a-3p also produce many isomiRs in many of the 32 analyzed cancers. OV in the case of miR-21-5p, and LAML in the case of miR-30a-3p are notable exceptions to this observation. Analogously, we also observed several miRNA arms that produce numerous isomiRs in some cancers only. The 5p and 3p arms of miR-9 are a characteristic such example: both arms produce numerous isomiRs in LGG.

Figure 1B:
Figure 1C:
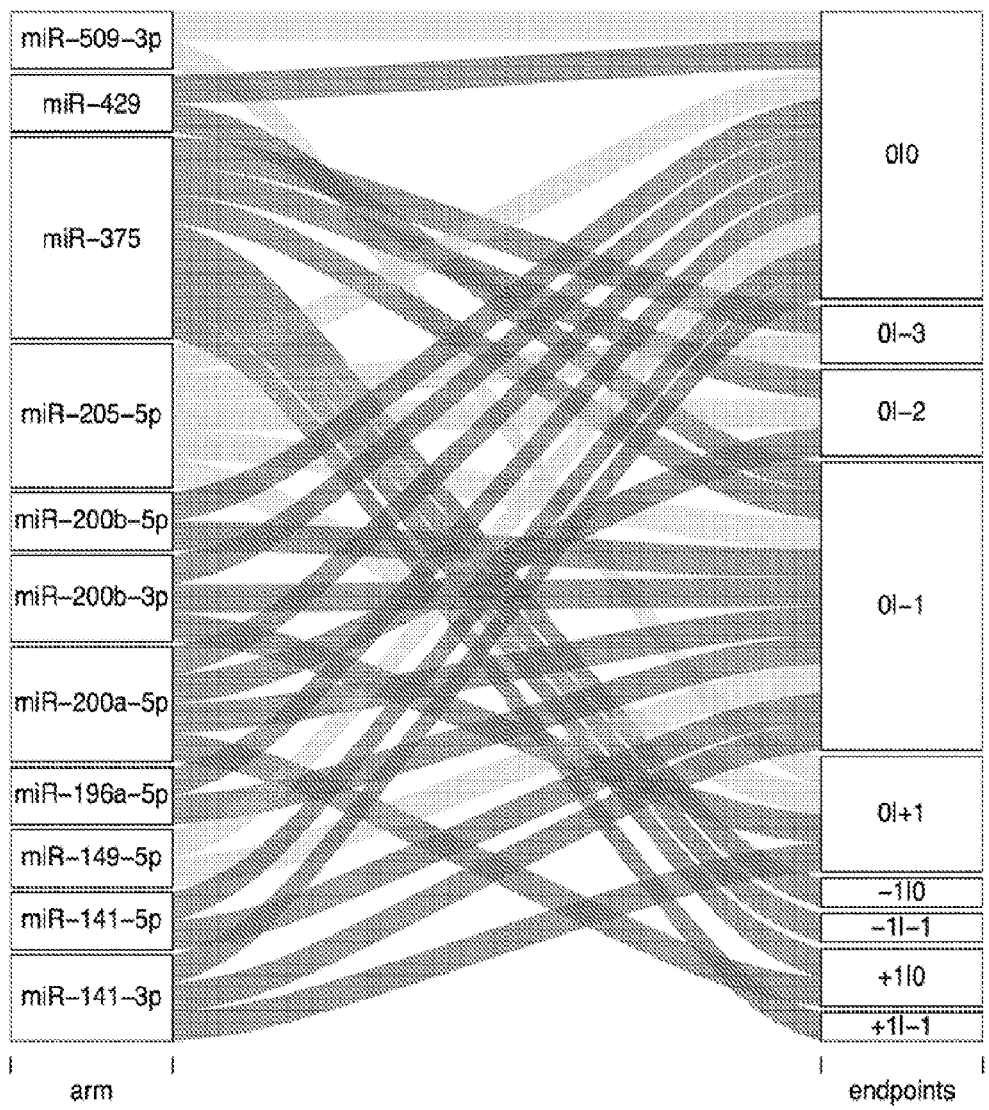

The Binarized IsomiR Profiles Reveal Cancer-Dependent Production of Abundant IsomiRs We studied systematically the binarized differences of presence/absence of abundant isomiRs among cancers by conducting all possible pairwise comparisons among 32 cancers. For each comparison, we performed $x^2$ tests, suitable for comparison of binarized data, for all isomiRs in the two given cancers. To focus on the most discriminatory isomiRs, we imposed a False Discovery Rate (FDR) threshold of 0.1% and further required that the percentage of samples in each cancer that contain the isomiR differ by at least 80%. We were able to identify several isomiRs that were significantly present in one cancer and absent from many of the remaining ones (FIG. 7). FIG. 1B illustrates this observation using LGG as an example. As already mentioned above (FIG. 1A), isomiRs from the miR-9-3p arm are present in LGG samples and absent from nearly all other cancers. The opposite holds true for isomiRs from the miR-10a-5p arm and the miR-200 family: they are absent from LGG and present in 71-93% of the other cancers. Another characteristic example can be seen in FIG. 1A: in TGCT, there is significant presence of many isomiRs from the miR-302 family that are absent from nearly all other cancers.

MiRNA-Arm Transcription is Also Cancer-Dependent

Noticing the co-presence/co-absence of isomiRs from the same miRNA arm in some cancers, we tested the hypothesis that the miRNA arms themselves are also differentially present among cancer types. We repeated the previous $X^2$ analysis for the binarized profiles of miRNA arms (see above for definitions) and were able to largely replicate the results that we obtained at the isomiR level. COAD provides a characteristic example. At the isomiR level, several isomiRs from the miR-215-5p arm were found to be COAD-specific when compared to the other cancer types. Looking at miRNA arms only, we find that the 5p arm of miR-215 also exhibits the same trend, i.e. its production of isomiRs is specific to COAD.

Hierarchical Clustering of Cancers Using Binarized IsomiR Profiles

Figure 1D:
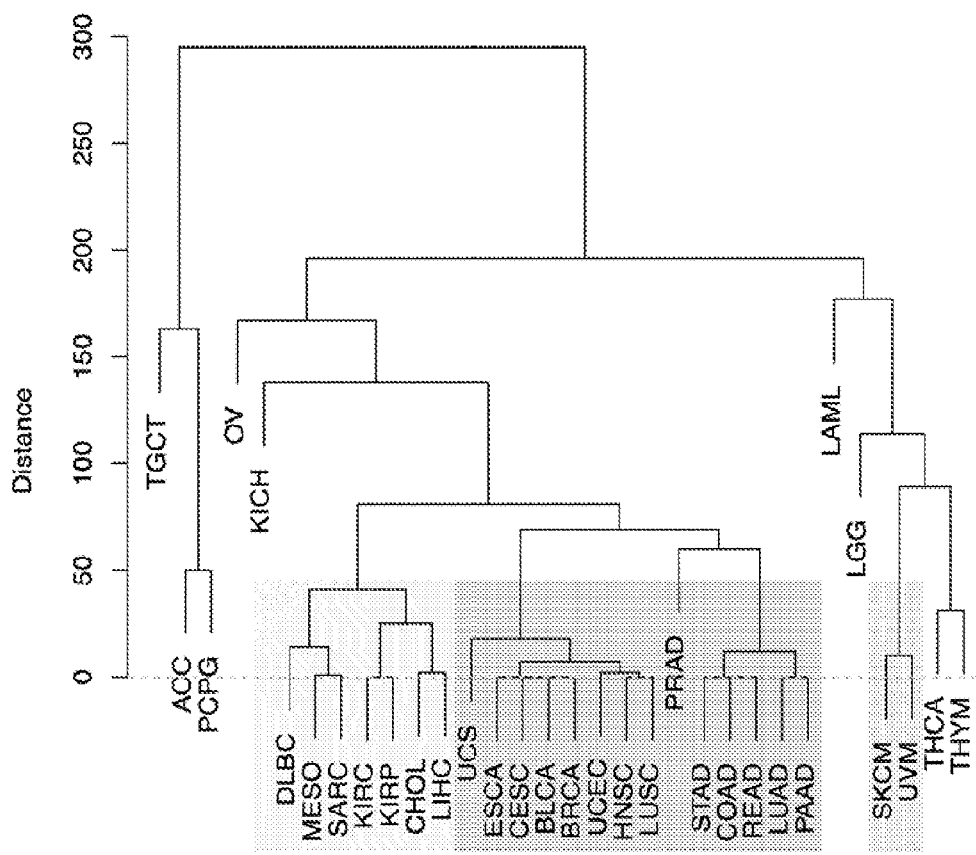

First, we examined how well we can classify the 32 cancer types using binarized isomiR profiles and hierarchical clustering (HCL). As a distance metric between two cancers, we used the Hamming distance between the respective binarized isomiR profiles. Essentially this measures the isomiR differences (present→absent, absent→present) between the two cancers being compared. The resulting dendrogram is shown in FIG. 1D. In it we observe several interesting clusters. A first cluster contains almost all the adenocarcinomas, like PAAD and PRAD. A second cluster encloses the BRCA and BLCA cancer types along with LUSC and head and neck HNSC. A third cluster includes cancers of the kidneys (KIRC, KIRP), liver (LIHC) and the bile duct (CHOL). We also note the clustering of the two melanomas (UVM, SKCM).

The above clustering into tumor groups implies a small Hamming distance and indicates similarities in the profiles of abundant isomiRs. By extension, the profile similarities imply commonalities in the respective molecular physiologies. However, this univariate analysis is not suitable for tackling the multidimensional question of cancer classification.

Conventional Multivariate Clustering Cannot Separate all Cancer Types

Figure 2A:
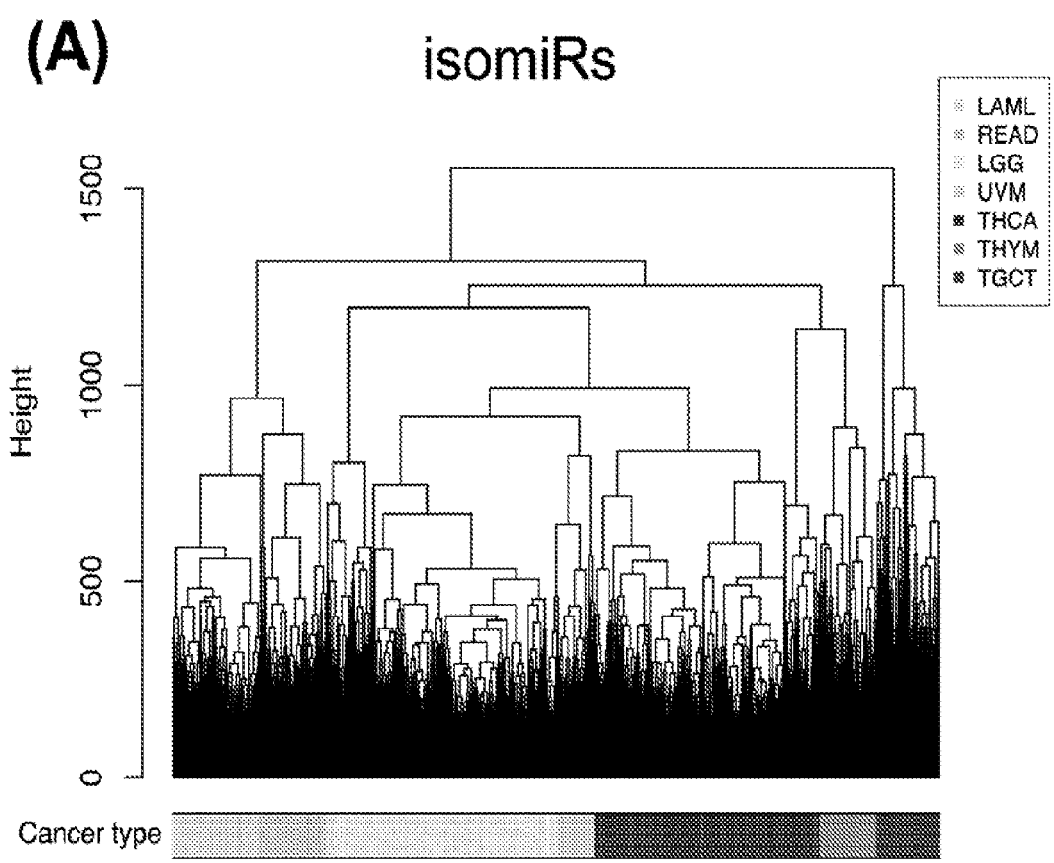
FIGS. 2A-2D illustrate multivariate hierarchical clustering on the binarized expression vectors. (A and B) Hierarchical clustering (hamming distance as metric) on the isomiR (A) or miRNA arm (B) profile of samples from different cancer types. The leaves of the dendrogram are tumor types. (C and D) Networks of all potential pairwise discriminations using hierarchical clustering (hamming distance as metric) on the isomiR (C) or miRNA arm profile (D). Two nodes (cancers) are connected if and only if the corresponding samples were found to form two separate clusters, with the samples of one cancer clustered distinctly from the other.
Figure 2B:
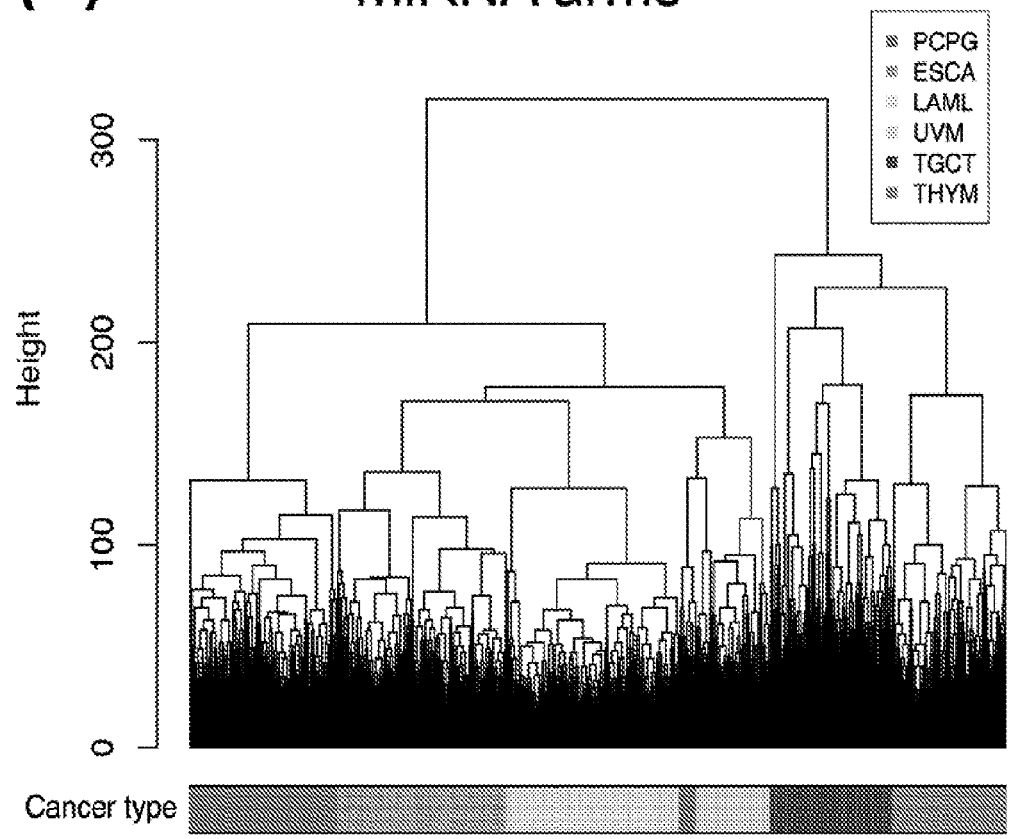

We next embark on multivariate statistical approaches to evaluate the hypothesis that the binarized isomiR and binarized miRNA-arm abundance profiles can be used for tumor discrimination and classification. After computing Hamming distances between pairs of samples (not pairs of cancers) using the respective binarized isomiR profiles, we carried out HCL. We were able to discriminate up to seven cancers using the binarized isomiR profiles (FIG. 2A). Collapsing isomiR profiles into binarized miRNA-arm profiles did not provide any additional discriminatory ability (FIG. 2B). Accordingly, use of HCL and Hamming distances alone, provides for the ability to discern some, but not all cancer types.

Figure 2C:
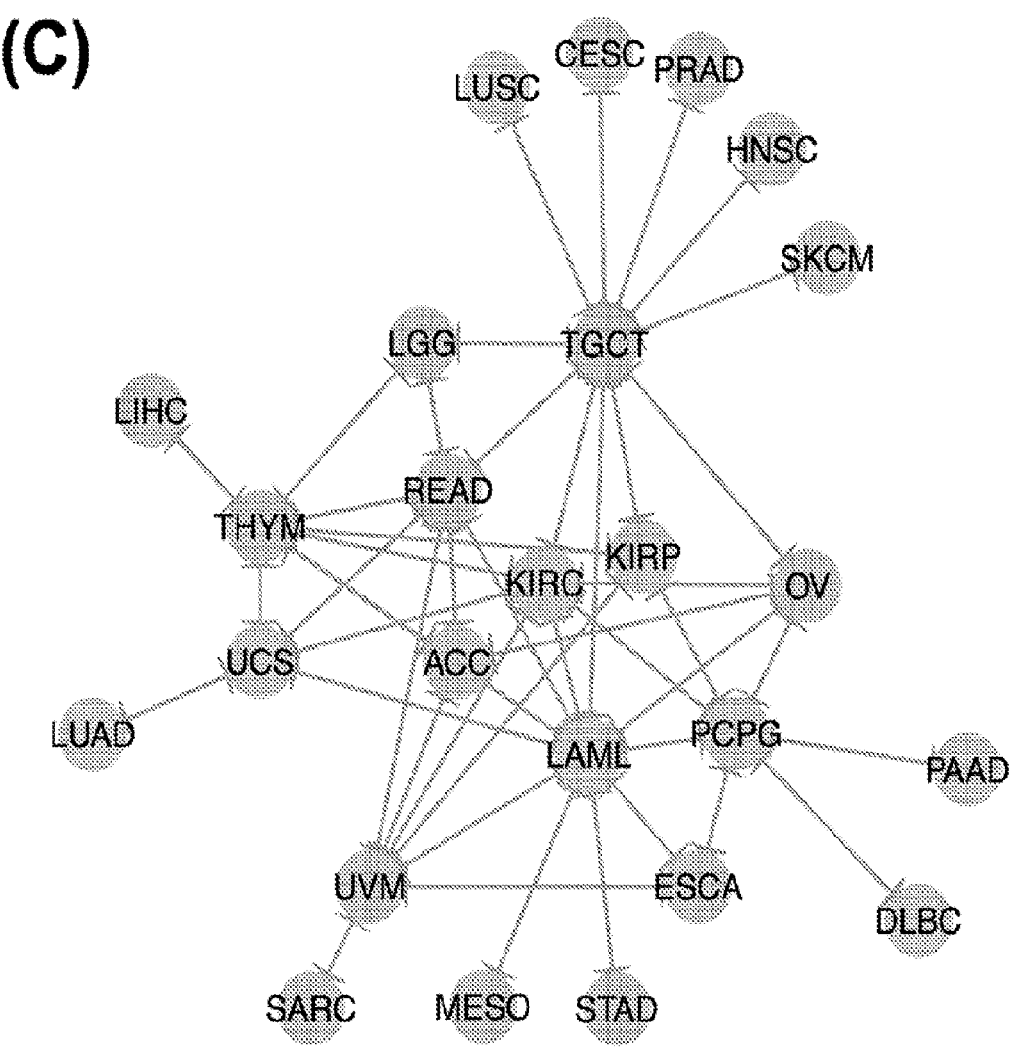
Figure 2D:
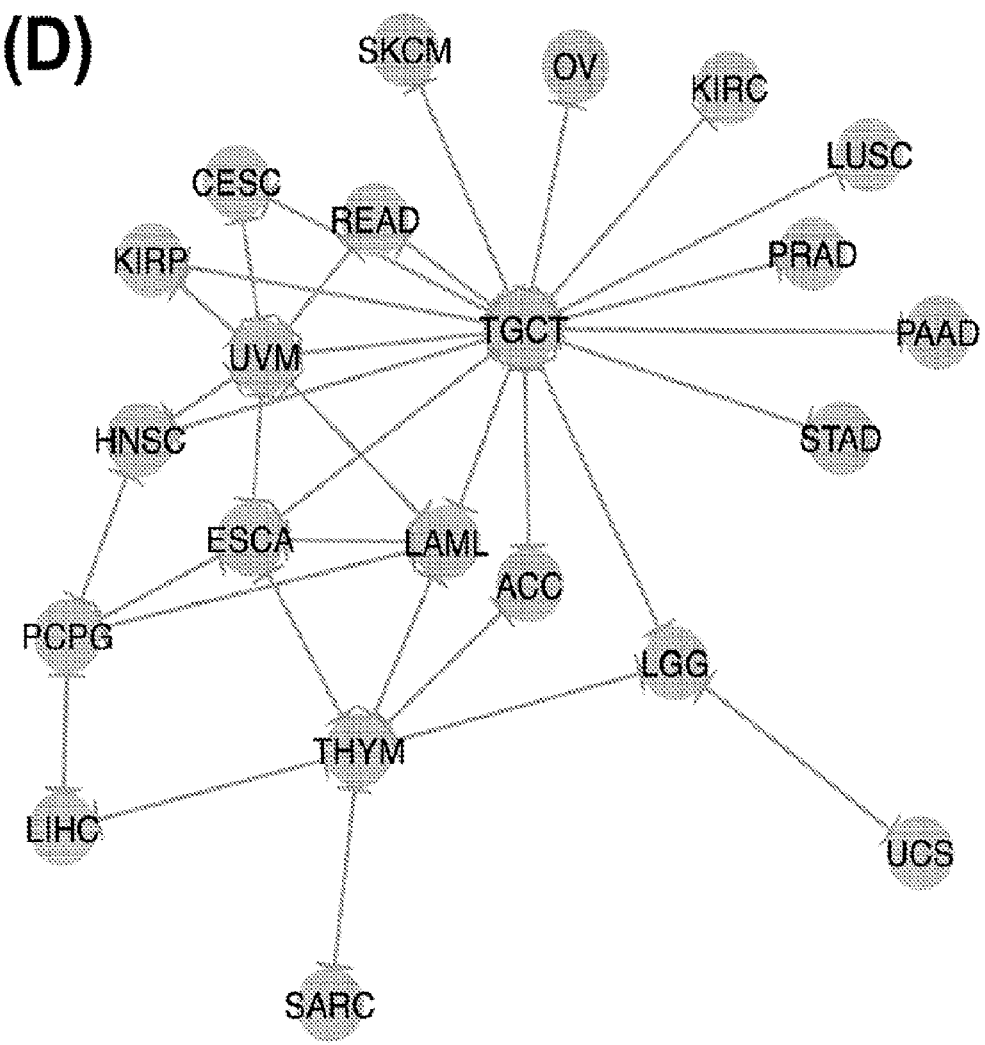

To investigate the upper limit of using HCL and Hamming distances at the sample level, we considered all possible cancer pairs and performed all comparisons among the respective samples. In each case, we examined whether each cancer's samples would form their own cluster. FIGS. 2C (isomiRs) and 2D (miRNA arms) illustrate the outcome of this analysis. In the shown networks, each node is a cancer type. Two nodes are linked with an edge if and only if the corresponding cancers can be distinguished from one another (large Hamming distance between samples from the respective cancers). LAML, TGCT, and THYM appear as central hubs in these networks: this means that these cancers can be distinguished with relative ease from several other cancer types. We note the absence of nodes for e.g. COAD and THCA from these networks. This indicates that, using the current clustering model (Hamming distance+HCL), COAD and THCA cannot be distinguished from other cancers. Also, not surprisingly, binarized isomiR profiles (FIG. 2C) can separate several more cancers from one another compared to binarized miRNA-arm profiles (FIG. 2D).

SVMs Built on Binarized Profiles can Discriminate Among Cancers

SVMs have been gaining popularity thanks to their ability to do multi-class classification in many different contexts (41-45). SVMs are intrinsically designed for binary classifications, i.e. for finding the best hyperplane that separates two a priori defined clusters. For our multi-cancer classification, we used an approach analogous to PhyloPythia, our method for classifying metagenomes (41,42). In particular, we build 496 SVMs for each of all possible "cancer-type-X vs. cancer-type-Y" pairwise comparisons, and, then, integrate the information into a single model by attaching probabilities to the classification outcome. This number is generated by 32*31/2=496, which identifies all unique pairs of 32 distinct items.

We split our 9,291 tumor datasets into training sets (used to construct each model) and test sets (used to evaluate each model), as is general practice in machine learning. Specifically, for each cancer type in turn, we formed a training set that comprised 60% of the type's samples. The remaining 40% of the samples for the cancer type at hand formed the test set. For each cancer type, we used the respective "training" samples to build an SVM aimed at separating the cancer type at hand from the remaining cancer types.

We built 496 SVM models using the "binarized isomiR profiles" and another 496 models using the "binarized miRNA-arm profiles." The isomiR SVM models were evaluated separately from the miRNA-arm SVM models. For the 496 SVM models being considered, we presented each test sample to each of the 496 SVMs in turn and used their output to build a 32-dimensional vector of probabilities: the i-th element of the vector is the probability that the test sample at hand belongs to the i-th cancer type. We imposed a probability threshold of 0.5: if the i-th element of the probability vector was ≥0.5 then the test sample was classified as belonging to the i-th cancer type. If none of the 32 probabilities reached the 0.5 level, then, the test sample was assigned to the 'Other' category. The 'Other' category contains false negatives as well as samples that truly do not belong to the 32 considered cancer types.

Figure 3A:
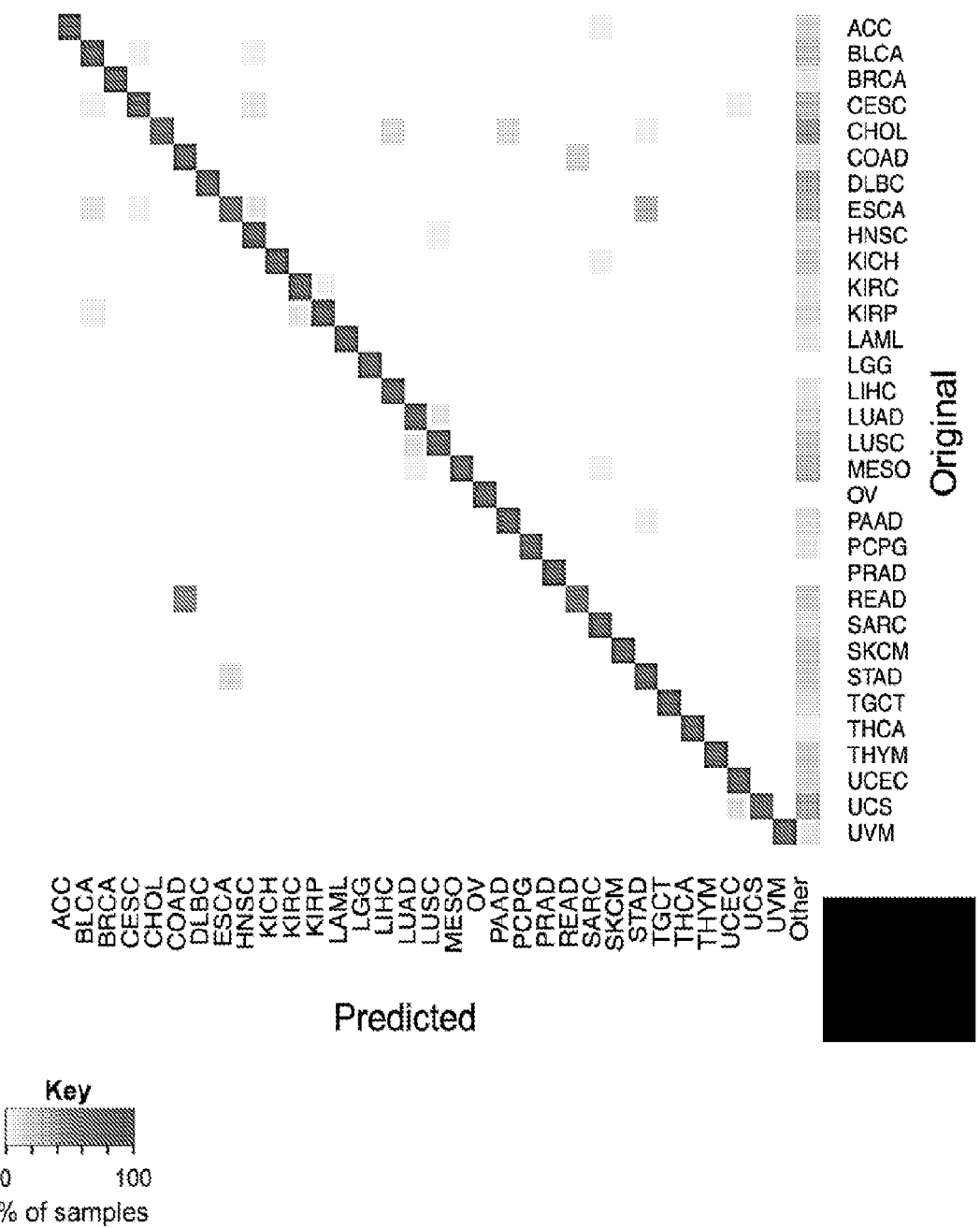
FIGS. 3A-3D illustrate how Support Vector Machines (SVM) correctly classify 32 cancer types. SVM classification using the binarized isomiR (A) or the binarized miRNA arm (B) expression profile. Each row of the heatmap represents the original cancer class and each column the predicted cancer class. The shading of each cell in the heatmap is proportional to the percentage (%) of samples originally as the cancer type in the respective row to be predicted as the cancer type of the respective column. The % is calculated as the average across 1,000 iterations. (C-D) Sensitivity (C) and FDR (D) scores for the SVM models built using the binarized isomiR (darker gray) or miRNA arm (lighter gray) expression profiles.

The SVM model building and testing cycle was repeated for a total of 1,000 times. In each iteration, we used a different set of randomly selected samples for training. FIG. 3A shows a heatmap that summarizes the average prediction performance of the SVMs that are based on the binarized isomiR profiles. Each row designates the cancer type to which the test sample belongs and each column designates the predicted cancer type. A perfectly-specific classifier should not generate any non-diagonal entries. A perfectly-sensitive classifier should not generate any entries in the "Other" category. As can be seen, the binarized isomiR profiles can clearly discriminate among cancer types and to correctly classify each sample to its correct origin. There is one notable instance of seemingly diminished performance that involves several rectum tumors (READ) that were misclassified as COAD tumors. In reality, this is not unexpected considering that READ and COAD tumors are molecularly similar and their distinction is largely driven by anatomy (46).

Figure 3B:
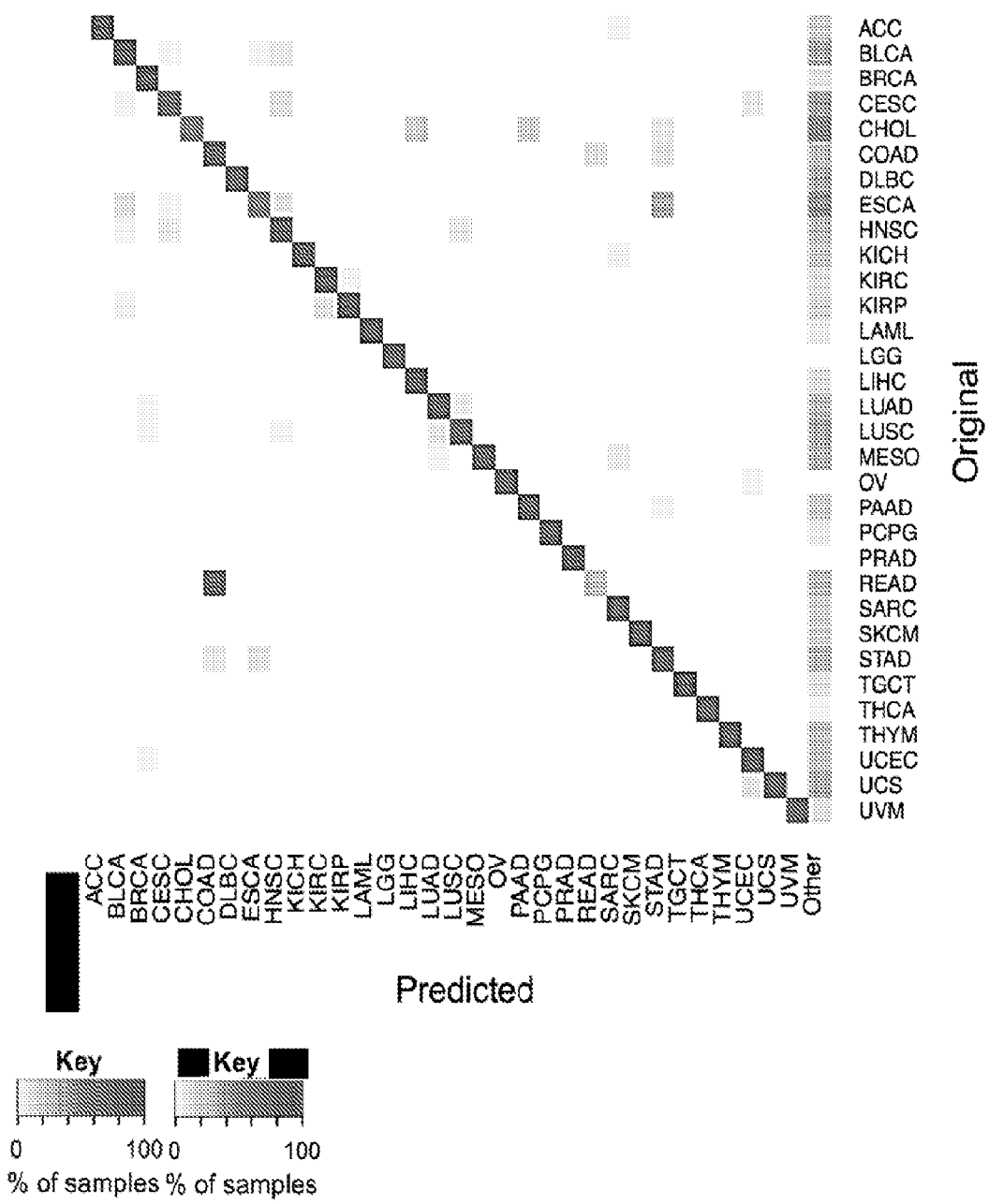

FIG. 3B shows an analogous heatmap that summarizes the average prediction performance of the SVMs that are built using the binarized miRNA-arm profiles. As can be seen, the classification remains largely successful. This suggests that simply interrogating whether a miRNA arm produces isomiRs can provide good performance when classifying cancer samples.

Figure 3C:
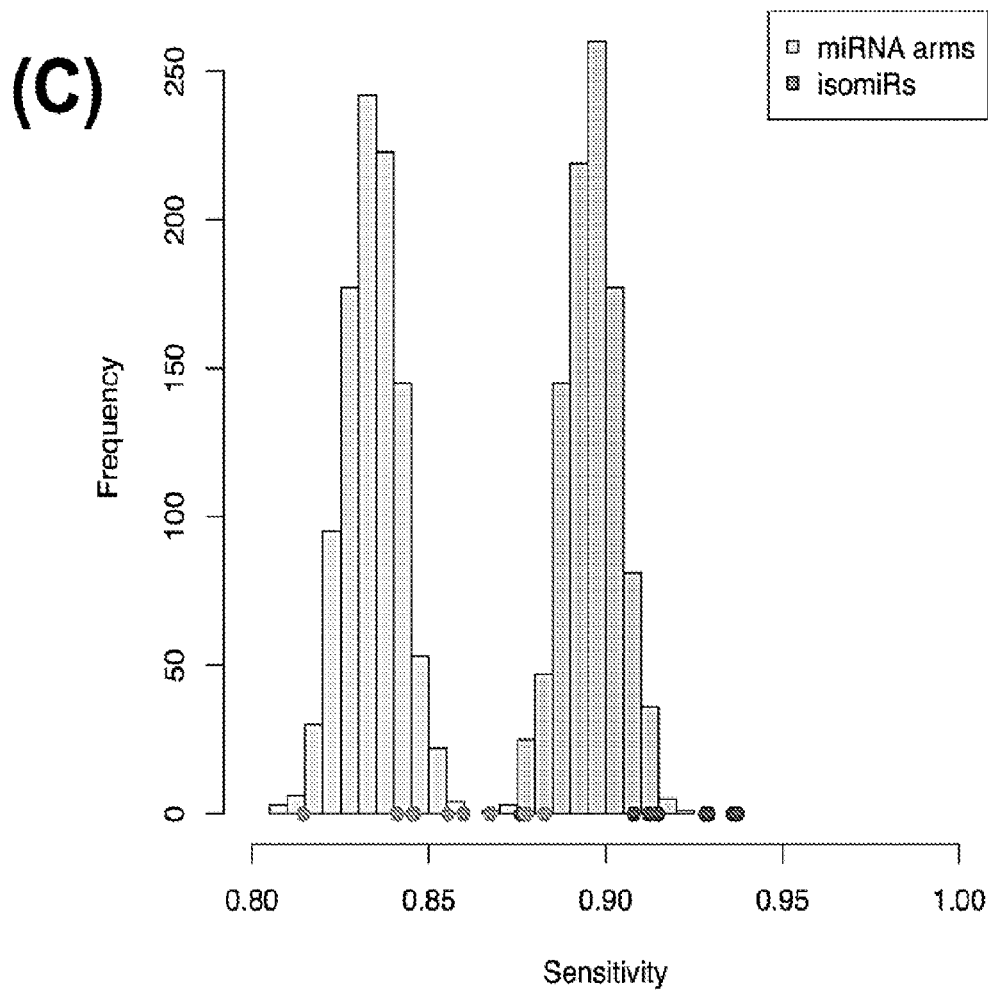
Figure 3D:
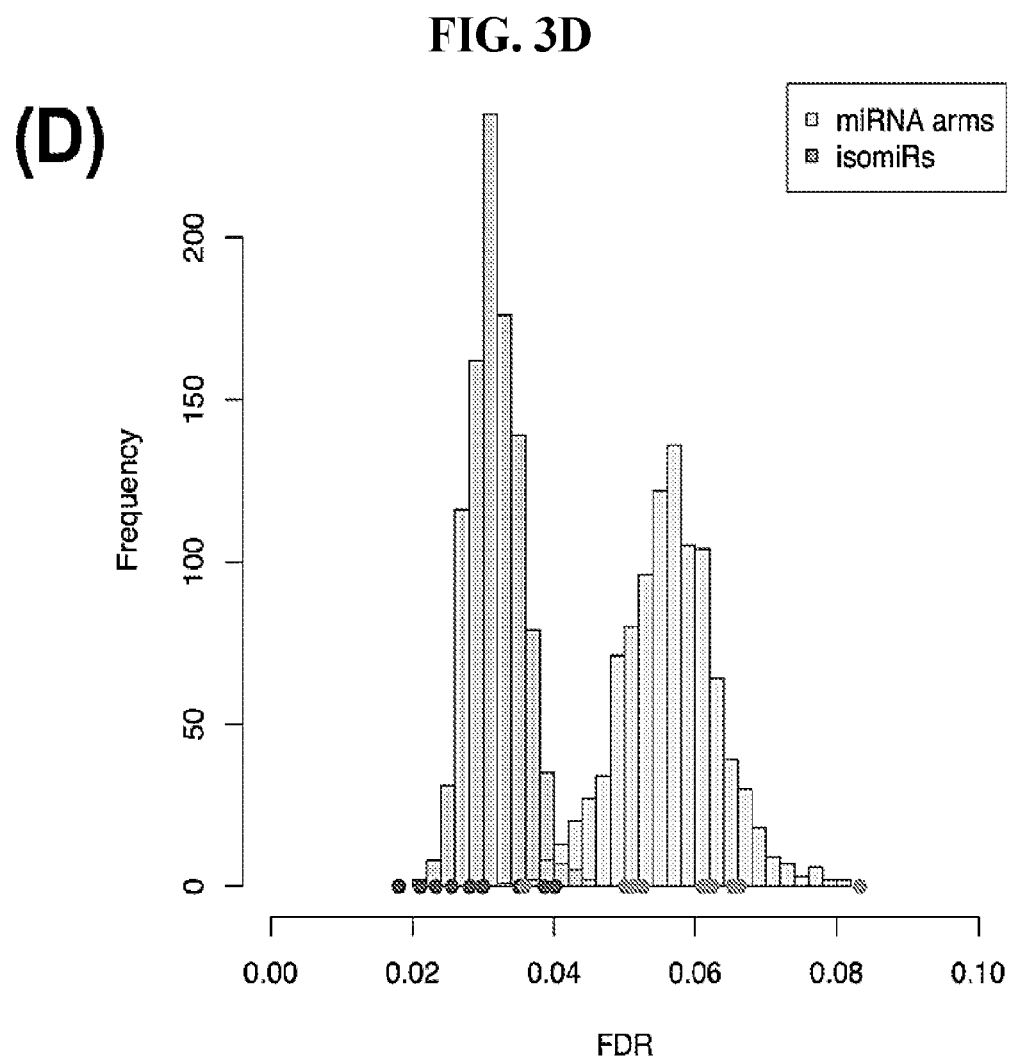

Finally, we quantified the performance of the 1,000 SVM models by building the distribution of the respective sensitivity and FDR scores. We did this separately for the binarized isomiR and miRNA-arm SVM models. FIG. 3C shows the resulting distributions for sensitivity and FIG. 3D for FDR. It is evident that binarized isomiR profiles are considerably more effective in correctly classifying tumor samples showing a mean sensitivity score of 93%. Even though lower (87%), the average sensitivity of the SVMs that were based on the binarized miRNA-arm profiles is fairly high in absolute terms. Indeed, one should consider here the magnitude of the task and how little information is actually used in this case when building these SVM models. The FDR scores also supported the effectiveness of the SVM-based classification. Specifically, the binarized isomiR profiles exhibited a mean FDR of 3%, while the binarized miRNA arm profiles one of 5%.

Validating the Resulting SVM Classification

To validate that the achieved SVM classification is not artificial, we carried out two tests. In the first test, we kept the number of 'present' isomiRs constant but randomly rearranged them in each sample. Then proceeded with building our 1,000 isomiR-based SVM models and testing them with the "correct" test samples. As expected, all of the test samples, in all 1,000 iterations, were assigned to the 'Other' category.

In the second test, we shuffled the labels of the training samples prior to training each SVM model with the binarized isomiR profile. As before, we built 1,000 SVM models and tested them with the "correct" test samples. As before, doing so resulted in the complete collapse of the model.

Based on the outcome of these two tests, we conclude that the classification results depicted in FIG. 3 are not driven by random or accidental events. Instead, the binarized isomiR and miRNA-arm profiles appear to carry actionable information. Accordingly, as described in the methods here, we can utilize these binarized isomiR and miRNA-arm profiles to classify a particular sample as pertaining to a specific cancer type. Upon classification, treatment of that patient can be tailored to the particular therapeutic that targets that specific cancer.

The Most Discriminatory IsomiRs and miRNA Arms are not Among Those Frequently-Studied As the SVM attempts to identify the best-separating hyperplane in the multidimensional space, some of the features are given more weight than others. In our case, these features would be tantamount to specific isomiRs and specific miRNA arms respectively.

To identify those isomiRs that were deemed most significant in separating the various cancer types, we ran the SVM method using as training set the whole TCGA dataset and extracted the variable importance (VI) score for each variable as the mean of the squares of the feature weights (47) of all pair-wise comparisons. We repeated the same analysis for miRNA arms and identified those with the highest VI values.

Among the isomiRs, we found that two isomiRs from the 5p arm of miR-205 were deemed most important by the isomiR-based SVM classifiers. These were followed by several isomiRs from both arms of miR-141. Notably, we observed a trend for agreement between the SVM models built on isomiR profiles and miRNA-arm profiles respectively with regard to the miRNA loci that the two models deem important. The loci include miR-205, miR-141, and miR-200c.

To validate these findings, we used the RandomForest algorithm, which has been shown able to identify significant variables for classification (48). We found the VI scores from RandomForest to be strongly and positively correlated with the VI scores from the SVM models: Spearman rho correlation coefficient 0.886 (P-val<0.01). The correlation improves further to 0.932 (P-val<0.01) when we compare the VI scores obtained from the binarized miRNA-arm models. The fact that a second independent algorithm validates the SVM conclusions adds further support to the relevance of using binarized profiles.

Figure 4A:
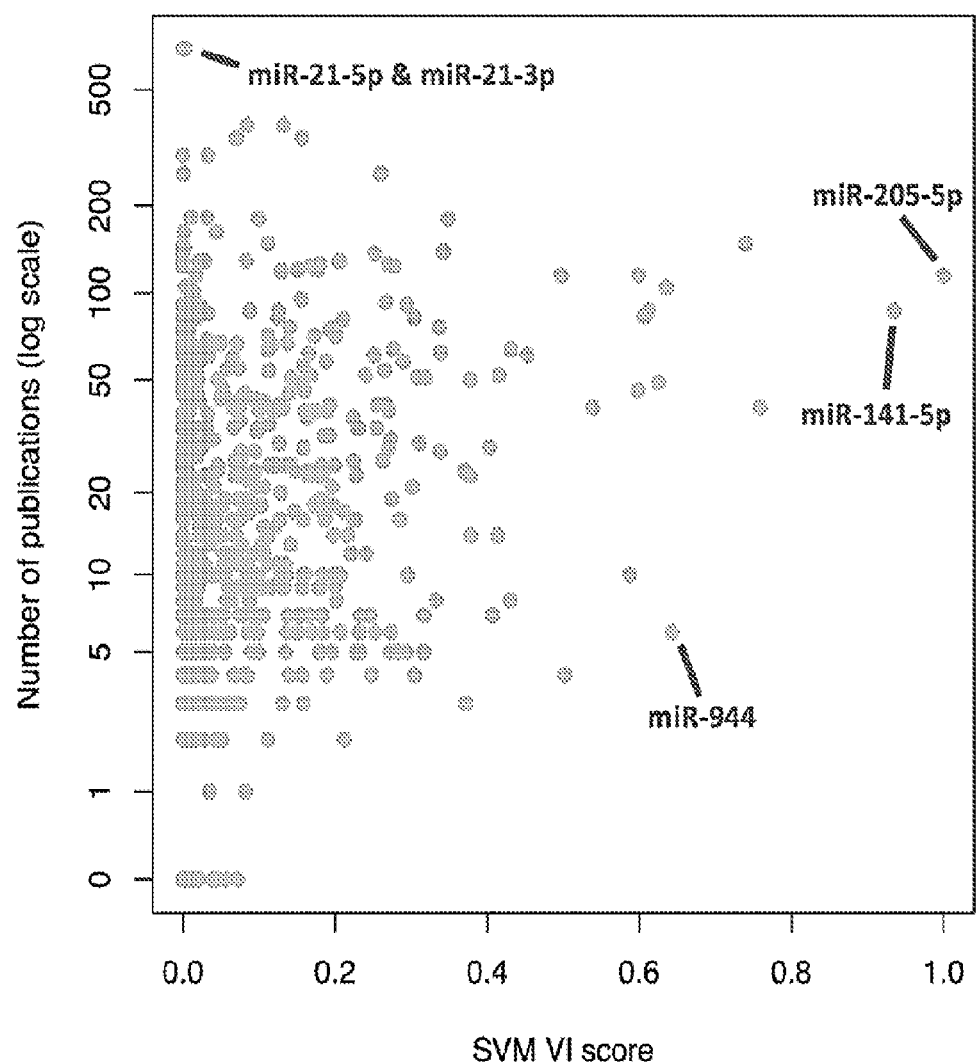
FIGS. 4A-4B illustrate how the number of publications does not correlate with the importance of a feature for classification purposes. (A) Number of publications against the variable importance (VI) score as calculated from the SVM classification model based on miRNA arms. Spearman correlation coefficient=0.303. (B) Number of publications with the word "biomarker" or "signature" in their title against the "variable importance" (VI) score as calculated from the same SVM. Spearman correlation coefficient=0.123.
Figure 4B:
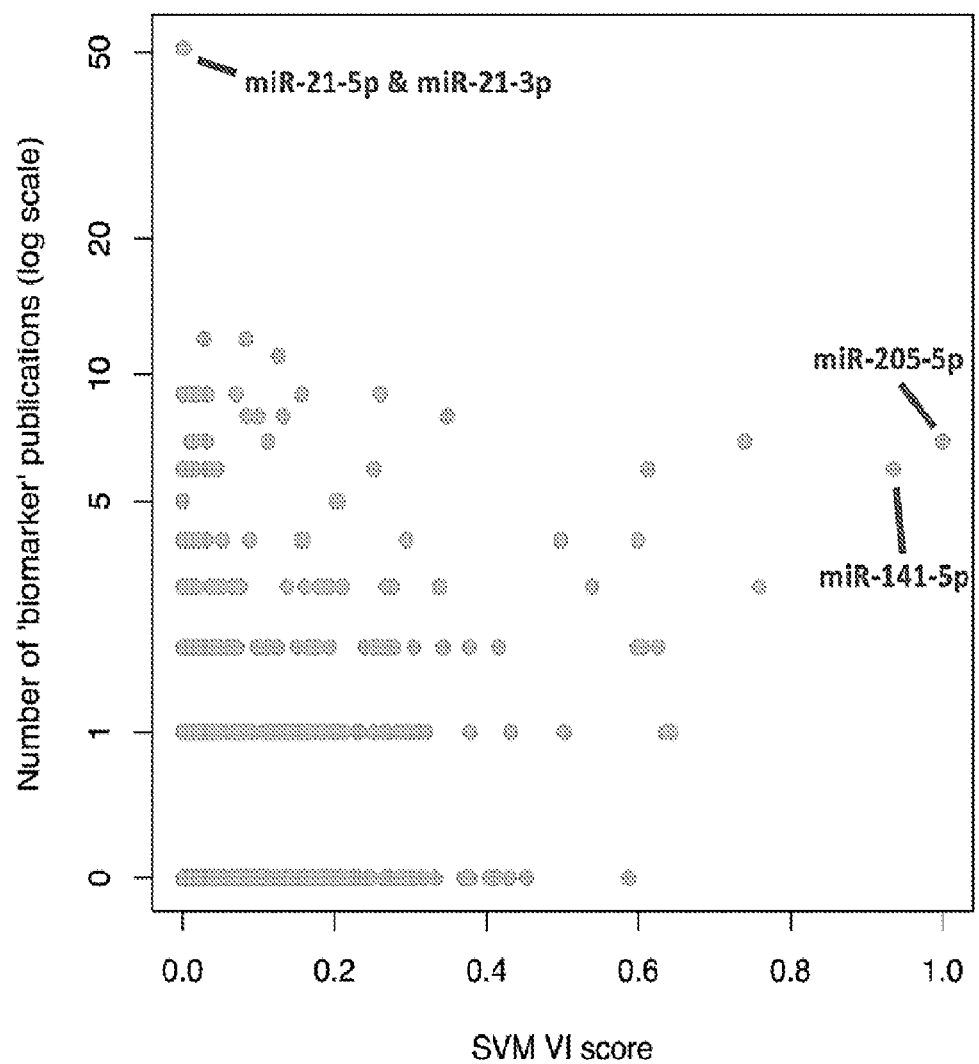

Having confirmed with two independent machine-learning tools the VI scores, we associated the corresponding molecules with the number of PubMed. For this step, we specifically used those miRNA loci that have entries in the Gene database of NCBI and retrieved the number of Pubmed entries associated with each miRNA gene. FIG. 4A shows the result of this association for SVMs using binarized isomiRs as features. FIG. 4B shows the result of this association for SVMs using binarized miRNA arms as features. We observed a mean of 52 publications per isomiR and 30 publications per miRNA arm. A striking result of this analysis is that both arms of the mir-21 precursor are each associated with the highest number of publications. However, with regard to their ability to classify cancer samples, both the SVM and RandomForest models assign miR-21 a considerably low VI score (little discriminatory power). It is also important to underline that both the SVMs and the RandomForest deemed miR-944 to be among the most important miRNAs for cancer classification: miR-944 currently has only six PubMed entries (FIG. 4). Other examples of discriminatory miRNAs with few PubMed entries include miR-429 (87 entries), miR-192 (46 entries), miR-194 (10 entries), and miR-135b (40 entries).

Lastly, we repeated the above analysis with one change. Specifically, we examined the correlation of the VI score with the number of times that the isomiR, or miRNA arm respectively, is found to differentially present in a pairwise comparison. We found that the isomiRs and miRNA arms that had the most impact on cancer classification were the ones that were found to be differentially present among many cancer types and not the ones that were uniquely present or absent in one cancer type. Similar results were obtained for both isomiRs and miRNA arms under the RandomForest model as well.

Summarily, the above findings suggest that the current body of literature is somewhat limited in regards to studies of miRNAs with the potential to be cancer-specific biomarkers.

The Ability to Classify with SVMs Trained on Binarized Profiles Remains when Only a Reduced Set of Features is Used The above-mentioned SVM and RandomForest models considered all 7,466 present isomiRs (isomiR profiles) or all 807 present miRNA arms (miRNA-arm profiles). As we discussed in the previous section, the various isomiRs and miRNA-arms have variable value in cancer classification. Based on these observations, we investigated the possibility that we could obtain reasonable classification results using a reduced set comprising the most important features (isomiRs or miRNA arms, FIGS. 5A and 5B, respectively). By reducing the number of classifications, we can dramatically reduce the cost and time required to make a determination.

Figure 5A:
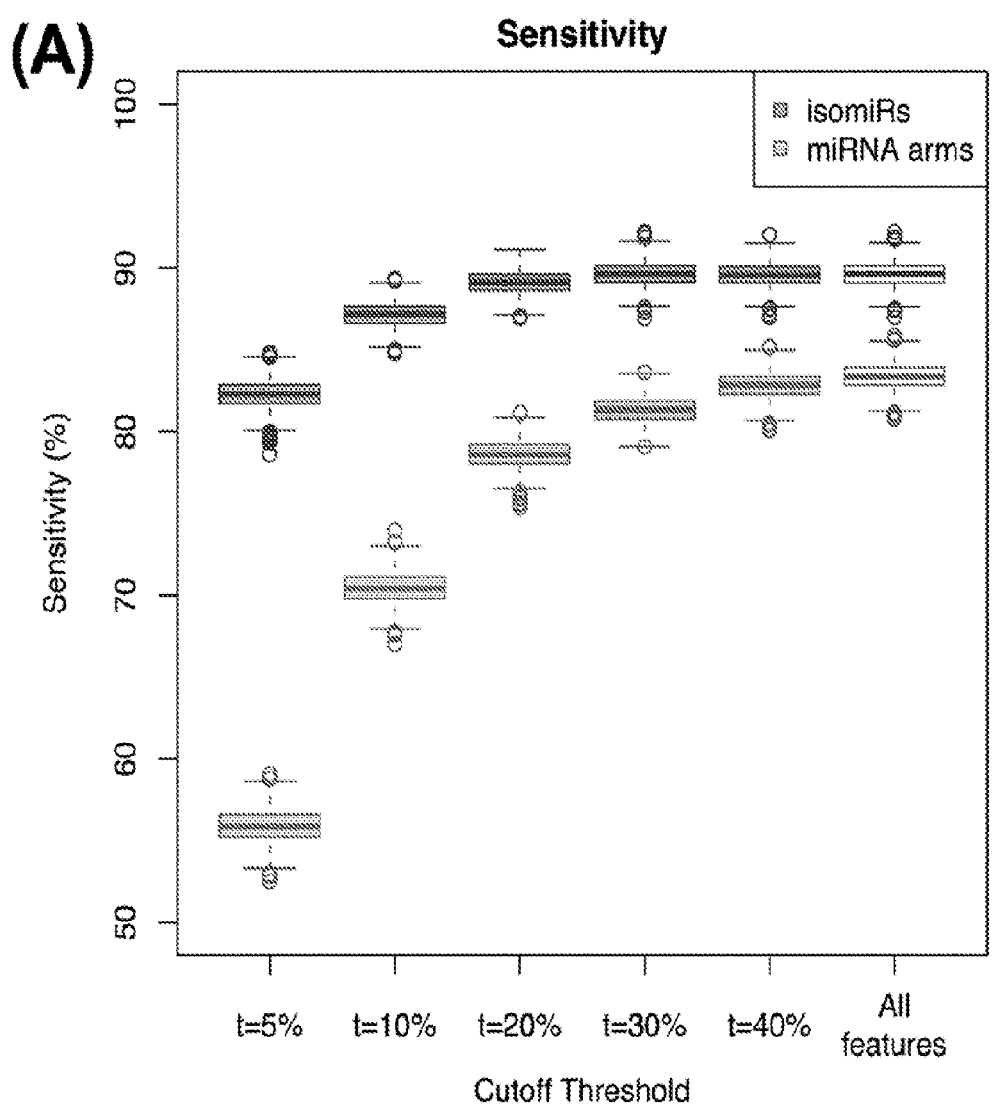
FIGS. 5A-5B illustrate how the sensitivity and FDR of SVM classification change when reduced lists of features are used. The plots correspond to the case of a classifier that is built to distinguish among 32 cancers. (A) Boxplots showing sensitivity for isomiRs (dark gray) and miRNA arms (light gray). (B) Analogous boxplots showing the FDR for the corresponding SVM, for isomiRs (dark gray) and miRNA arms (light gray).
Figure 5B:
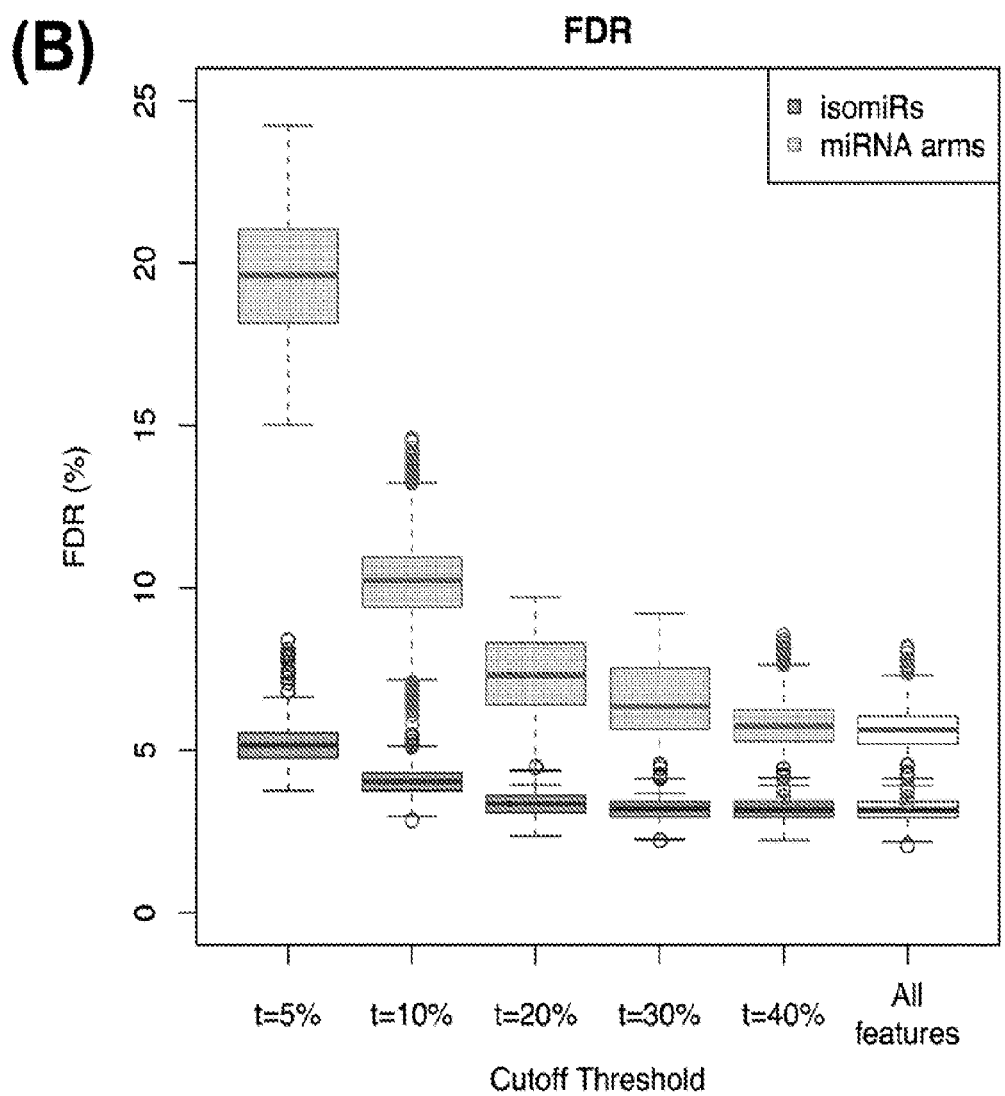

We used the top 456 isomiRs and repeated the multi-cancer SVM-based training and classification. We found that even with this reduced set of isomiR features we maintained our ability to correctly classify samples—the concomitant sensitivity following 1,000 training/testing iterations decreased to 82% (FIG. 5A) and the FDR increased by a mere of 2% to 5% (FIG. 5B). Much of the error originated from the higher uncertainty of the method to classify samples, as evidenced by the higher number of samples clustered as "Other."

We also repeated the analysis using a reduced set of most important miRNA-arm features to build our SVM models. We intersected the top 10% most important miRNA arms of the SVM model with the top 10% miRNA arms of the RandomForest and obtained 47 arms. This signature of miRNA arms was sufficient to classify the samples to their respective cancer type (FIG. 5A) at the expense of a modest penalty in sensitivity (decreased to 70% from 83% when all features were used) and FDR (increased to 10% from 6% when all features were used, as seen in FIG. 5B). These results suggest that the reduced set of miRNA arm features retains a considerable ability to classify cancer samples, albeit it does not reach the levels achieved by isomiRs. On the other hand, the miRNA-arm-based SVMs achieve these results using ten times fewer features than isomiRs.

Clinical Studies

In this study, we described the usefulness of the binarized isomiR and miRNA arm profile in multiple cancer types. We based our work on previous observations that tissue-specific expression profiles exist (28, 29, 37, 49) and tissue and cell type differences can be adequately described by only the presence or absence of RNA transcripts (39, 40). We were centered on isomiRs, as our previous work was able to justify the importance of these molecules (31, 35) and their contribution to better understand BRCA heterogeneity (31). Therefore, our over-arching goal was to investigate how well binarized profiles of isomiRs and miRNA arms describe cancer types. To this end, we leveraged the TCGA datasets due to the standardized protocols and data availability (36).

After fixing several caveats on the reported profiles, including multiple counting (36), we first identified several instances of cancer-specific expression or cancer-specific loss of expression of several isomiRs and their corresponding arms. The most striking example is miR-9 and its isomiRs that are uniquely present in LGG tumor samples.

This miRNA is highly expressed in the nervous system and has evident important roles in neuronal development and diseases (50, 51) supporting our findings of its tissue-specificity. Another miRNA that also exhibited similar characteristics in LGG was miR-219 and, intriguingly, this miRNA has been implicated in neural differentiation processes (52). We were also able to identify additional miRNAs that have almost unique expression in some tissues, like the liver-specific arms of miR-122 (53). Our unbiased and global approach also identifies potential cancer-type-specific miRNAs, like miR-671 in ovarian cancer or our novel miRNA ID00737-3p in THCA (Supplementary Tables S3 and S4—as provided in Application No. 62/411,417). OV was also an interesting case as it had a relatively high number of isomiRs and miRNA arms absent as compared to other cancer types. The opposite was, however, true for TGCT tumor samples that exhibited unique presence of several isomiRs and arms, especially from the miR-302 family (Supplementary Tables S3 and S4—as provided in Application No. 62/411,417), that has been shown to be important in pluripotency of stem cells and cell reprogramming (54, 55).

Causative links for the above observations cannot be identified based on our analysis. The cancer-specific expression can also not be guaranteed, as the isomiRs and the miRNA arms can preserve tissue-specific expression trajectories, even in the cancerous state. Indeed, cellular context matters in cancer biology (56) and may contribute to cancer-type differences. As the TCGA projects were largely focused on tumor classifications, limited normal samples were analyzed. Further studies with balanced numbers of normal samples will be needed to decouple the "normal" from the "cancer" signal, as done previously but with a considerably smaller sample size (28). Focusing on tissue specific molecules is of great importance here. On the other hand, miRNAs that are ubiquitously expressed in multiple tissues are not very informative. For example, miR-21-5p, the miRNA with the highest number of publications, and several members of the let-7 family are present in all the samples and all the cancer types of our study. This characteristic means these miRNAs would not be useful in pinpointing a patient's ailing tissue, which would be a prerequisite for a specific therapy recommendation (57). Towards this direction, several recent studies suggest the use of panels of miRNAs rather than single molecules for biomarkers (58-60).

Having established that qualitative differences among cancer types exist and are meaningful, we next employed multivariate and machine learning tools to build classification models and predict the cancer type solely based on binarized expression information of isomiRs or miRNA arms. We found that SVMs that are built using binarized isomiR profiles were capable of correctly predicting the cancer class with 90% sensitivity and 3% FDR (FIG. 3). The performance of SVMs that use isomiRs was better than SVMs that use miRNA arms as features and persisted when reducing the isomiR vector one order of magnitude (FIGS. 5A and 5B). Independent evidence of higher discriminatory power of isomiRs against miRNA arms is limited but start to emerge. In a recent work, Koppers-Lalic et al. found that miRNA isoforms are able to improve the specificity for prostate cancer detection, including isomiRs from the miR-204-5p, miR-21-5p and miR-375-3p arms (61). In addition, our previous work in breast cancer showed that isomiRs can better distinguish normal breast tissue from BRCA tumors as compared to archetype miRNAs (35). Potential reasons for the higher predictive value of isomiRs can be that quantification and modeling at the miRNA arm level is inherently bound to lose information, especially information rooted in biological mechanisms that can specifically affect isomiR levels (62-64).

A Case for miRNA-Arm-Based Approaches

Despite the evident superiority of using isomiRs as features, one can envision situations where cost and efficiency are important considerations. In such cases, employing an miRNA-arm-based classifier, instead of an isomiR-based one, represents a reasonable compromise between sensitivity and specificity.

For many years, quantification of short molecules like miRNAs has been relying on methodologies that do not attempt to guarantee the target molecule's endpoints. This is not surprising considering that until very recently scientists had no reason to suspect that the production of isomiRs is, in fact, constitutive in nature. Consequently, such methodologies would simultaneously amplify, and, thus, quantify as an aggregate the multiple isoforms of a short molecule, if the sequences of these isoforms differed from one another only a little. Methodologies that have been very popular with users include Affymetrix's Expression Arrays®, Nanostring's nCounter®, and other.

In light of the findings described in FIGS. 3 and 5, quantification assays that allow us to declare a miRNA arm as present without any regard to which isomiRs specifically are produced from that arm represent an opportunity. Ideally, one would like to use just enough assays to reach the plateau of sensitivity and FDR. The data in FIGS. 5A and 5B suggest that between 115 and 198 miRNA-arm features will achieve this goal. Importantly, such a classifier could be implemented by using the existing, off-the-shelf assays that have been used all along to quantify molecules in the pre-isoform era. In other words, an easy-to-put-together, reasonably-well-performing, reasonably-low-cost solution is within reach and would not require any additional development costs.

A further embodiment is directed towards a method for classifying cancer using miRNA arms using between 10% and 40% of all arms provided by the methods described herein.

In preferred embodiments, it is preferable to use between 20% and 30% of all the isomiRs or miRNA arms.

One such case that we studied in depth was that of STAD. Here, we began by posing the following slightly-different question: "can we determine whether this sample belong to STAD and not to any of the remaining 31 cancer types?" Again, we used SVMs to build a classifier to answer this question.

Figure 9A:
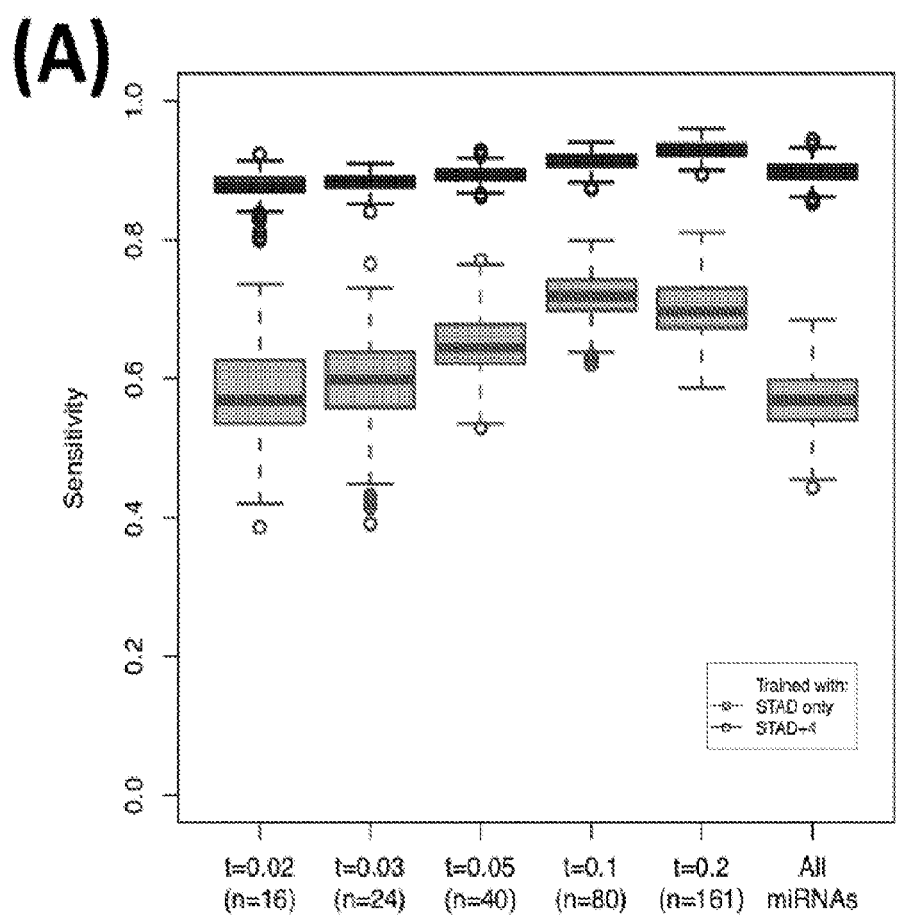
FIGS. 9A-C illustrate how the sensitivity and FDR of SVM classification change when reduced lists of features are used. The plots correspond to the case of a classifier that is built using the arms of miRNAs as features and aimed at specifically identifying STAD samples (light gray) or STAD+ESCA+PAAD+COAD+READ samples (dark gray). Shown are Sensitivity (A), Specificity (B) and False Discovery Rate (C) for the classifier (n=400 iterations) trained with all the miRNAs (righmost boxes on each plot) or a subset of the most discriminatory miRNAs (rest of the boxes) as identified by the runs with all the molecules.
Figure 9B:
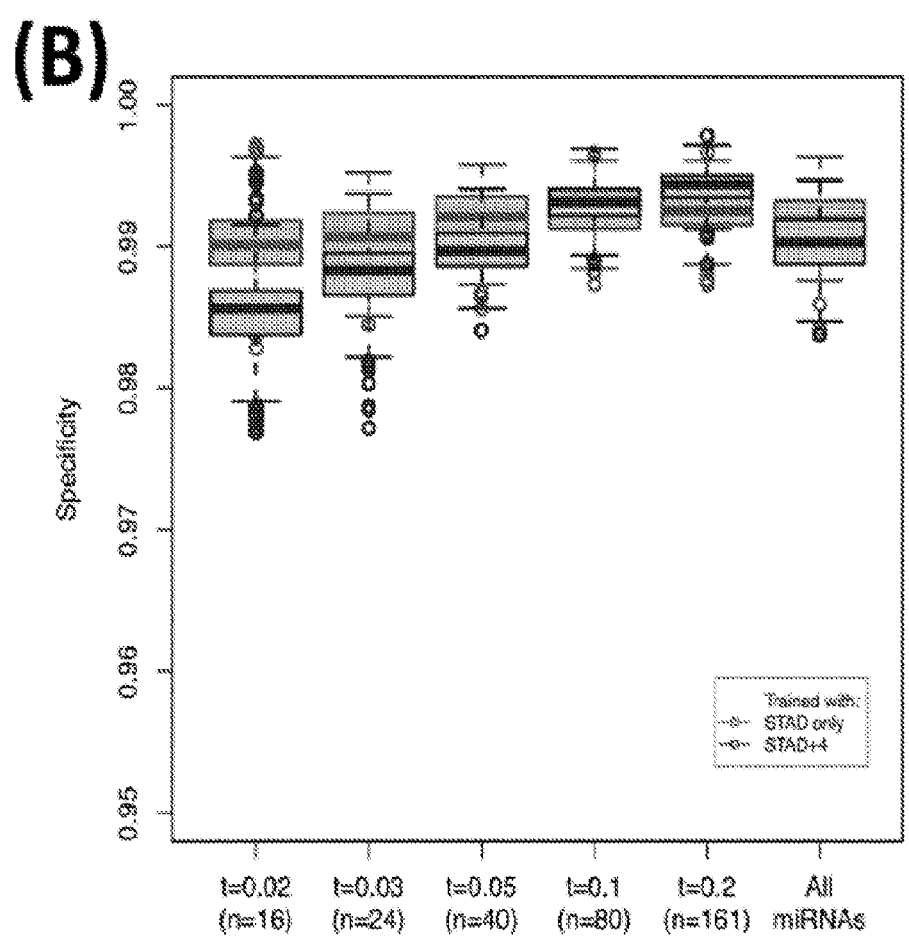
Figure 9C:
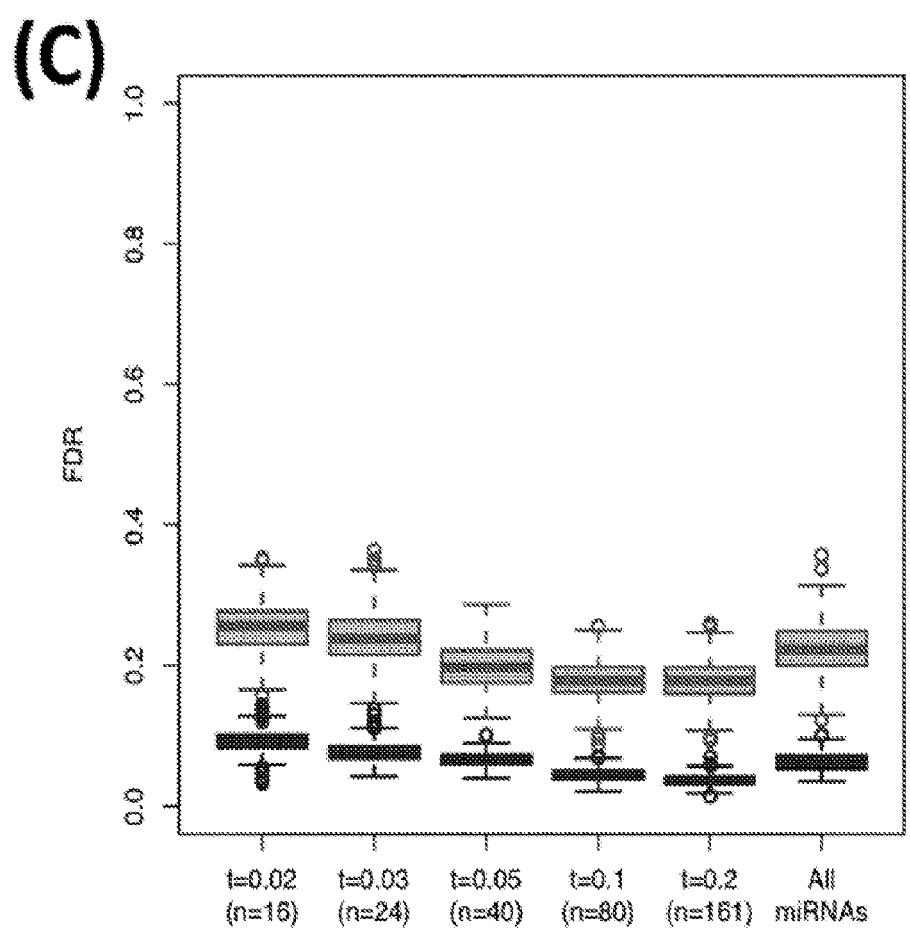

As features we used binarized miRNA-precursor arms. The resulting model's sensitivity was around 60%, i.e. much lower than the original 83% that we achieved with the binarized miRNA-precursor arms when we tackled the 32-way classification question (light gray boxes in FIG. 9A). Nonetheless, the classifier's specificity was high whereas its FDR was around 23% (light gray boxes in FIGS. 9B and 9C).

The low sensitivity was rather surprising considering that the classifier was now tackling a 2-way classification problem, instead of the original 32-way one. We suspected that some of the 31 non-STAD cancers had "STAD-like" isomiR profiles. These other profiles were likely "confusing" the classifier.

In light of these observations, we rebuilt our SVM classifier by identifying the few cancers that were most similar to STAD. There were four cancer types that had no differentially present miRNA arm when compared to STAD ([65]). It turns out that all four cancers belong to the gastrointestinal tract. The four cancers that are most similar to STAD are: ESCA, PAAD, COAD, and READ, i.e. esophageal, pancreatic, stomach, colon, and rectum cancers, respectively.

In light of this finding, we pitted these five cancers (STAD, ESCA, PAAD, COAD, READ) against the remaining 27 cancers. The resulting sensitivity, specificity, and FDR (dark gray boxes in FIGS. 9A-C, respectively) of the new classifier were markedly improved. The sensitivity again reached 90% whereas the FDR dropped to 6%.

We also studied the quality of the classification by training with increasing numbers of binarized miRNA-precursor arm features. Specifically, we ranked the features in order of decreasing VI, i.e. in order of decreasing ability to discriminate. We then selected and trained using 16, 24, 40, 80, 161 and all miRNA arms, respectively. The performance (sensitivity, specificity, and FDR) in each case can be seen in FIGS. 9A-C. As is evident, using only 16 miRNA arms as features to train a classifier in the case of STAD+ESCA+PAAD+COAD+READ vs. 27 cancers allows us to achieve a high sensitivity (90%) with a small FDR.

Even though our analyses and the building of the new classifier were driven by our initial focus on STAD, the resulting system could also be used for labeling samples that may belong to ESCA, PAAD, COAD, or READ. To this end, we used the approach that we described in the previous paragraph to evaluate the sensitivity, specificity, and FDR of the classifier when it is presented with samples from each of these four cancers in turn. The table below shows the results. With the exception of ESCA, the classifier performs really well in each case. Of particular note here is the case of PAAD (pancreatic ductal adenocarcinoma), an aggressive type of cancer for which there is an urgent need for diagnostics and therapeutics.

|  | Sensitivity | Specificity | FDR |
| --- | --- | --- | --- |
| COAD | 98.1 +/− 1.1 | 99.9 +/− 0.0 | 1.2 +/− 0.9 |
| READ | 96.7 +/− 2.2 | 100.0 +/− 0.0 | 1.7 +/− 1.9 |
| PAAD | 91.0 +/− 4.0 | 99.9 +/− 0.0 | 4.0 +/− 2.4 |
| ESCA | 57.7 +/− 5.8 | 99.7 +/− 0.1 | 19.2 +/− 5.6 |
| STAD | 92.4 +/− 1.9 | 99.7 +/− 0.1 | 5.0 +/− 1.6 |

Therapeutic Treatments and Testing

A patient presents herself at the physician's office with chest pain. After an examination, the physician recommends imaging. The latter reveals a mass in the individual's liver. A biopsy confirms the presence of cancer. However, the tissue of origin is inconclusive, thus making treatment difficult.

Accordingly, we took a clinical sample and processed the obtained clinical sample, to extract total RNA from it. We performed quality control on the extracted RNA to verify that it is appropriate for further processing. Then, taking a portion of the extracted RNA, we performed a series of reactions to isolate the short RNA molecules and prepare them appropriately for deep sequencing.

Upon completion of the sequencing, we retrieved all the sequenced reads, and processed them to identify the quantity of each present molecule. Then, we binarized the expression profile: all isomiRs with abundances in the top 20% were considered 'present,' and 'absent' otherwise. Subsequently, we processed this profile with the SVM classifier whose performance is summarized in FIG. 5.

The classifier returns 32 probability scores whose sum is equal to 1. The i-th such score represents the probability that the sample belongs to the respective cancer type. We would choose the cancer type with the highest probability only if this probability exceeded 0.5. If not, then we would conclude that there is not enough signal that would allow an unambiguous classification. A review of the particular sample reveals that the classifier is pretty confident returning a computed probability for "OV" that is well above 0.5: our patient has "ovarian cancer" and paclitaxel is administered to the patient for treatment.

Those of skill in the art will recognize that determination of the cancer leads to a specific and particular therapeutic for treating the metastatic cancer cells.

Assaying Small Collections of Target Molecules

To employ a classifier that is based on isomiRs one can envision a scenario where, for example, deep-sequencing is used to quantify the isomiRs that make up the classifier. Deep sequencing is clearly a much more costly proposition when is interested only in a handful of isomiRs. In such a situation, one can envision a custom-designed molecular "panel" that includes "probes" that specifically quantify only a handful of isomiRs of interest. Each one of these probes will need to exhibit both 5' and 3' endpoint specificity, namely be able to quantify the target isomiR while being as un-responsive as possible to other isomiRs that may be present in the milieu and differ from the target isomiR at either the 5' terminus, the 3' terminus, or both. A technology that is potentially applicable here is "dumbbell-PCR" [66]. Also, the miR-ID method [67] could be adapted for use with isomiRs. It is conceivable that other similar approaches will also become available in the future and could be used as well. Designing assays that are sensitive to changes in the target molecule's endpoints is feasible but their optimization may require a lot of effort. Thus, one consideration in selecting such a method is its scalability characteristics.

More on "Meta-Arms"

As we mentioned above, some isomiRs may have ambiguous origins. I.e. there may be multiple miRNA loci from which they could be originating. This becomes a consideration when we use miRNA arms as features of the classifier because it requires that we combine the potential genomic sources into a single entity. While the "label" by which we refer to such an entity is unique, the "sequence" that we can attach to it may not be necessarily. This is due to the fact that although the corresponding miRNA arms share the sequence segment that matches the isomiR, the sequences of the miRNA arms that contain the isomiR can differ. For example, the isomiR GCGCTTCC combined with CTTTGGAG could be originating from either GGAAAAGAA combined with

GGCGCTTCC combined with

CTTTGGAG combined with TGTTA (the 3p arm of miR-524, which is not among the list of sequences included in this application) or from

AAAAGAAGGCGCTTCCCTTTGGAGTGTTA (the 3p arm of miR-525, which is listed as SEQ ID NO. 8015). Since the goal is to be able to capture all such sequences we have introduced a regular expression notation that makes use of square brackets '[' and ']' as follows. [AC] indicates that a specific position can be occupied by either an A or a C. An example is SEQ ID NO: 7468 whose sequence is

CTTCCCTTTGTCATCCT[AT][CT]GCCT[AG][AG].

The way to interpret it is that

CTTCCCTTTGTCATCCT, which is shown underlined in in the previous sentence, as a portion of SEQ ID No. 7468, can be followed by either A or T, which can be followed by C or T, which can be followed by GCCT, etc. Among the 8,595 sequences mentioned in this application there are 67 entries that fall in this category that comprise 43 distinct regular expressions.

The disclosure refers to citations, shown in parentheses, e.g. "(10)", which designate references listed below.

REFERENCES

1. Hood, L. and Rowen, L. (2013) The Human Genome Project: big science transforms biology and medicine. *Genome medicine*, 5, 79.
2. Veneziano, D., Di Bella, S., Nigita, G., Laganà, A., Ferro, A. and Croce, C. M. (2016) Noncoding RNA: Current Deep Sequencing Data Analysis Approaches and Challenges. *Hum. Mutat.*, 1-16.
3. Aalto, A. P. and Pasquinelli, A. E. (2012) Small noncoding RNAs mount a silent revolution in gene expression. *Current opinion in cell biology*, 24, 333-340.
4. Clark, M. B., Choudhary, A., Smith, M. A., Taft, R. J. and Mattick, J. S. (2013) The dark matter rises: the expanding world of regulatory RNAs. *Essays in biochemistry*, 54, 1-16.
5. Clerget, G., Abel, Y. and Rederstorff, M. (2015) Small non-coding RNAs: a quick look in the rearview mirror. *Methods in molecular biology*, 1296, 3-9.
6. Ha, M. and Kim, V. N. (2014) Regulation of microRNA biogenesis. *Nat Rev Mol Cell Biol*, 15, 509-524.
7. Winter, J., Jung, S., Keller, S., Gregory, R. I. and Diederichs, S. (2009) Many roads to maturity: microRNA biogenesis pathways and their regulation. *Nature cell biology*, 11, 228-234.
8. Bartel, D. P. (2004) MicroRNAs: genomics, biogenesis, mechanism, and function. *Cell*, 116, 281-297.
9. Bartel, D. P. (2009) MicroRNAs: target recognition and regulatory functions. *Cell*, 136, 215-233.
10. Schirle, N. T., Sheu-Gruttadauria, J. and MacRae, I. J. (2014) Structural basis for microRNA targeting. *Science*, 346, 608-613.
11. Lee, R. C., Feinbaum, R. L. and Ambros, V. (1993) The C. elegans heterochronic gene lin-4 encodes small RNAs with antisense complementarity to lin-14. *Cell*, 75, 843-854.
12. Reinhart, B. J., Slack, F. J., Basson, M., Pasquinelli, A. E., Bettinger, J. C., Rougvie, A. E., Horvitz, H. R. and Ruvkun, G. (2000) The 21-nucleotide let-7 RNA regulates developmental timing in Caenorhabditis elegans. *Nature*, 403, 901-906.
13. Sparks, E., Wachsman, G. and Benfey, P. N. (2013) Spatiotemporal signalling in plant development. *Nature reviews. Genetics*, 14, 631-644.
14. Dumortier, O., Fabris, G. and Van Obberghen, E. (2016) Shaping and preserving beta-cell identity with microRNAs. *Diabetes, obesity & metabolism*, 18 Suppl 1, 51-57.
15. Hilz, S., Modzelewski, A. J., Cohen, P. E. and Grimson, A. (2016) The roles of microRNAs and siRNAs in mammalian spermatogenesis. *Development*, 143, 3061-3073.
16. Edelstein, L. C., McKenzie, S. E., Shaw, C., Holinstat, M. A., Kunapuli, S. P. and Bray, P. F. (2013) MicroRNAs in platelet production and activation. *Journal of thrombosis and haemostasis: JTH*, 11 Suppl 1, 340-350.
17. Flowers, E., Won, G. Y. and Fukuoka, Y. (2015) MicroRNAs associated with exercise and diet: a systematic review. *Physiological genomics*, 47, 1-11.
18. Jeon, T. I. and Osborne, T. F. (2016) miRNA and cholesterol homeostasis. *Biochimica et biophysica acta*.
19. Mogilyansky, E. and Rigoutsos, I. (2013) The miR-17/92 cluster: a comprehensive update on its genomics, genetics, functions and increasingly important and numerous roles in health and disease. *Cell death and differentiation*, 20, 1603-1614.
20. Su, K., Zhang, T., Wang, Y. and Hao, G. (2016) Diagnostic and prognostic value of plasma microRNA-195 in patients with non-small cell lung cancer. *World journal of surgical oncology*, 14, 224.
21. Mehta, R., Otgonsuren, M., Younoszai, Z., Allawi, H., Raybuck, B. and Younossi, Z. (2016) Circulating miRNA in patients with non-alcoholic fatty liver disease and coronary artery disease. *BMJ open gastroenterology*, 3, e000096.
22. Calin, G. A. and Croce, C. M. (2006) MicroRNA signatures in human cancers. *Nature reviews. Cancer*, 6, 857-866.
23. Di Leva, G., Garofalo, M. and Croce, C. M. (2014) MicroRNAs in cancer. *Annual review of pathology*, 9, 287-314.
24. Backes, C., Kehl, T., Stockel, D., Fehlmann, T., Schneider, L., Meese, E., Lenhof, H. P. and Keller, A. (2016) miRPathDB: a new dictionary on microRNAs and target pathways. *Nucleic acids research*.
25. Cortez, M. A., Bueso-Ramos, C., Ferdin, J., Lopez-Berestein, G., Sood, A. K. and Calin, G. A. (2011) MicroRNAs in body fluids—the mix of hormones and biomarkers. *Nature reviews. Clinical oncology*, 8, 467-477.
26. Pimentel, F., Bonilla, P., Ravishankar, Y. G., Contag, A., Gopal, N., LaCour, S., Lee, T. and Niemz, A. (2015) Technology in MicroRNA Profiling: Circulating MicroRNAs as Noninvasive Cancer Biomarkers in Breast Cancer. *Journal of laboratory automation*, 20, 574-588.
27. Lu, J., Getz, G., Miska, E. A., Alvarez-Saavedra, E., Lamb, J., Peck, D., Sweet-Cordero, A., Ebert, B. L., Mak, R. H., Ferrando, A. A. et al. (2005) MicroRNA expression profiles classify human cancers. *Nature*, 435, 834-838.
28. Volinia, S., Calin, G. A., Liu, C. G., Ambs, S., Cimmino, A., Petrocca, F., Visone, R., Iorio, M., Roldo, C., Ferracin, M. et al. (2006) A microRNA expression signature of human solid tumors defines cancer gene targets. *Proceedings of the National Academy of Sciences of the United States of America*, 103, 2257-2261.

29. Rosenfeld, N., Aharonov, R., Meiri, E., Rosenwald, S., Spector, Y., Zepeniuk, M., Benjamin, H., Shabes, N., Tabak, S., Levy, A. et al. (2008) MicroRNAs accurately identify cancer tissue origin. *Nature biotechnology*, 26, 462-469.
30. Londin, E., Loher, P., Telonis, A. G., Quann, K., Clark, P., Jing, Y., Hatzimichael, E., Kirino, Y., Honda, S., Lally, M. et al. (2015) Analysis of 13 cell types reveals evidence for the expression of numerous novel primate- and tissue-specific microRNAs. *Proceedings of the National Academy of Sciences of the United States of America*.
31. Loher, P., Londin, E. R. and Rigoutsos, I. (2014) IsomiR Expression Profiles in Human Lymphoblastoid Cell Lines Exhibit Population and Gender Dependencies. *Oncotarget*, 5, 8790-8802.
32. Tan, G. C., Chan, E., Molnar, A., Sarkar, R., Alexieva, D., Isa, I. M., Robinson, S., Zhang, S., Ellis, P., Langford, C. F. et al. (2014) 5' isomiR variation is of functional and evolutionary importance. *Nucleic acids research*, 42, 9424-9435.
33. Wojcicka, A., Swierniak, M., Kornasiewicz, O., Gierlikowski, W., Maciag, M., Kolanowska, M., Kotlarek, M., Gornicka, B., Koperski, L., Niewinski, G. et al. (2014) Next generation sequencing reveals microRNA isoforms in liver cirrhosis and hepatocellular carcinoma. *The international journal of biochemistry & cell biology*, 53, 208-217.
34. Salem, O., Erdem, N., Jung, J., Munstermann, E., Worner, A., Wilhelm, H., Wiemann, S. and Korner, C. (2016) The highly expressed 5'isomiR of hsa-miR-140-3p contributes to the tumor-suppressive effects of miR-140 by reducing breast cancer proliferation and migration. *BMC genomics*, 17, 566.
35. Telonis, A. G., Loher, P., Jing, Y., Londin, E. and Rigoutsos, I. (2015) Beyond the one-locus-one-miRNA paradigm: microRNA isoforms enable deeper insights into breast cancer heterogeneity. *Nucleic acids research*, 43, 9158-9175.
36. Chu, A., Robertson, G., Brooks, D., Mungall, A. J., Birol, I., Coope, R., Ma, Y., Jones, S. and Marra, M. A. (2016) Large-scale profiling of microRNAs for The Cancer Genome Atlas. *Nucleic acids research*, 44, e3.
37. Landgraf, P., Rusu, M., Sheridan, R., Sewer, A., Iovino, N., Aravin, A., Pfeffer, S., Rice, A., Kamphorst, A. O., Landthaler, M. et al. (2007) A mammalian microRNA expression atlas based on small RNA library sequencing. *Cell*, 129, 1401-1414.
38. Shmulevich, I. and Zhang, W. (2002) Binary analysis and optimization-based normalization of gene expression data. *Bioinformatics*, 18, 555-565.
39. Tuna, S. and Niranjan, M. (2009) Classification with binary gene expressions. *Journal of Biomedical Science and Engineering*, 02, 390-399.
40. Zilliox, M. J. and Irizarry, R. A. (2007) A gene expression bar code for microarray data. *Nature methods*, 4, 911-913.
41. McHardy, A. C., Martin, H. G., Tsirigos, A., Hugenholtz, P. and Rigoutsos, I. (2007) Accurate phylogenetic classification of variable-length DNA fragments. *Nature methods*, 4, 63-72.
42. Warnecke, F., Luginbühl, P., Ivanova, N., Ghassemian, M., Richardson, T. H., Stege, J. T., Cayouette, M., McHardy, A. C., Djordjevic, G., Aboushadi, N. et al. (2007) Metagenomic and functional analysis of hindgut microbiota of a wood-feeding higher termite. *Nature*, 450, 560-565.
43. Noble, W. S. (2006) What is a support vector machine? *Nature biotechnology*, 24, 1565-1567.
44. Tsirigos, A. and Rigoutsos, I. (2005) A sensitive, support-vector-machine method for the detection of horizontal gene transfers in viral, archaeal and bacterial genomes. *Nucleic acids research*, 33, 3699-3707.
45. Yang, Z. R. (2004) Biological applications of support vector machines. *Briefings in bioinformatics*, 5, 328-338.
46. Cancer Genome Atlas, N. (2012) Comprehensive molecular characterization of human colon and rectal cancer. *Nature*, 487, 330-337.
47. Guyon, I., Weston, J., Barnhill, S. and Vapnik, V. (2002) *Machine Learning*, 46, 389-422.
48. Statnikov, A., Wang, L. and Aliferis, C. F. (2008) A comprehensive comparison of random forests and support vector machines for microarray-based cancer classification. *BMC bioinformatics*, 9, 319.
49. McCall, M. N., Jaffee, H. A., Zelisko, S. J., Sinha, N., Hooiveld, G., Irizarry, R. A. and Zilliox, M. J. (2014) The Gene Expression Barcode 3.0: improved data processing and mining tools. *Nucleic acids research*, 42, D938-943.
50. Yuva-Aydemir, Y., Simkin, A., Gascon, E. and Gao, F. B. (2011) MicroRNA-9: functional evolution of a conserved small regulatory RNA. *RNA biology*, 8, 557-564.
51. Coolen, M., Katz, S. and Bally-Cuif, L. (2013) miR-9: a versatile regulator of neurogenesis. *Frontiers in cellular neuroscience*, 7, 220.
52. Hudish, L. I., Galati, D. F., Ravanelli, A. M., Pearson, C. G., Huang, P. and Appel, B. (2016) miR-219 regulates neural progenitors by dampening apical Par protein-dependent Hedgehog signaling. *Development*, 143, 2292-2304.
53. Bandiera, S., Pfeffer, S., Baumert, T. F. and Zeisel, M. B. (2015) miR-122—a key factor and therapeutic target in liver disease. *Journal of hepatology*, 62, 448-457.
54. Gao, Z., Zhu, X. and Dou, Y. (2015) The miR-302/367 cluster: a comprehensive update on its evolution and functions. *Open biology*, 5, 150138.
55. Barroso-del Jesus, A., Lucena-Aguilar, G. and Menendez, P. (2009) The miR-302-367 cluster as a potential sternness regulator in ESCs. *Cell cycle*, 8, 394-398.
56. Schaefer, M. H. and Serrano, L. (2016) Cell type-specific properties and environment shape tissue specificity of cancer genes. *Scientific reports*, 6, 20707.
57. Shi, J. (2016) Considering Exosomal miR-21 as a Biomarker for Cancer. *Journal of clinical medicine*, 5.
58. Xin, H., Li, X., Yang, B., Zhang, L., Han, Z. and Han, C. (2014) Blood-based multiple-microRNA assay displays a better diagnostic performance than single-microRNA assay in the diagnosis of breast tumor. *Tumour biology: the journal of the International Society for Oncodevelopmental Biology and Medicine*, 35, 12635-12643.
59. Wang, Y., Liang, J., Di, C., Zhao, G. and Zhao, Y. (2014) Identification of miRNAs as potential new biomarkers for nervous system cancer. *Tumour biology: the journal of the International Society for Oncodevelopmental Biology and Medicine*, 35, 11631-11638.
60. Hornick, N. I., Huan, J., Doron, B., Goloviznina, N. A., Lapidus, J., Chang, B. H. and Kurre, P. (2015) Serum Exosome MicroRNA as a Minimally-Invasive Early Biomarker of AML. *Scientific reports*, 5, 11295.
61. Koppers-Lalic, D., Hackenberg, M., de Menezes, R., Misovic, B., Wachalska, M., Geldof, A., Zini, N., de Reijke, T., Wurdinger, T., Vis, A. et al. (2016) Noninvasive prostate cancer detection by measuring miRNA variants (isomiRs) in urine extracellular vesicles. *Oncotarget,* 7, 22566-22578.
62. Starega-Roslan, J., Witkos, T. M., Galka-Marciniak, P. and Krzyzosiak, W. J. (2015) Sequence features of Drosha and Dicer cleavage sites affect the complexity of isomiRs. *International journal of molecular sciences,* 16, 8110-8127.
63. Koppers-Lalic, D., Hackenberg, M., Bijnsdorp, I. V., van Eijndhoven, M. A., Sadek, P., Sie, D., Zini, N., Middeldorp, J. M., Ylstra, B., de Menezes, R. X. et al. (2014) Nontemplated nucleotide additions distinguish the small RNA composition in cells from exosomes. *Cell reports,* 8, 1649-1658.
64. Boele, J., Persson, H., Shin, J. W., Ishizu, Y., Newie, I. S., Sokilde, R., Hawkins, S. M., Coarfa, C., Ikeda, K., Takayama, K. et al. (2014) PAPD5-mediated 3' adenylation and subsequent degradation of miR-21 is disrupted in proliferative disease. *Proceedings of the National Academy of Sciences of the United States of America,* 111, 11467-11472.
65. Telonis A. G., Magee, R., Loher, P., Chervoneva, I., Londin, E., Rigoutsos, I. (2017) Knowledge about the presence or absence of miRNA isoforms (isomiRs) can successfully discriminate amongst 32 TCGA cancer types. *Nucleic Acids Res,* 45, 2973-2985.
66. Honda, S., Kirino, Y. (2015) Dumbbell-PCR: a method to quantify specific small RNA variants with a single nucleotide resolution at terminal sequences. *Nucleic Acids Res,* 43, e77.
67. Kumar, P., Johnston, B. H., Kazakov, S. A. (2011) miR-ID: a novel, circularization-based platform for detection of microRNAs. *RNA,* 17, 365-80.

Lengthy table referenced here

US11905563-20240220-T00001

Please refer to the end of the specification for access instructions.

Lengthy table referenced here

US11905563-20240220-T00002

Please refer to the end of the specification for access instructions.

LENGTHY TABLES

The patent contains a lengthy table section. A copy of the table is available in electronic form from the USPTO web site (https://seqdata.uspto.gov/?pageRequest=docDetail&DocID=US11905563B2). An electronic copy of the table will also be available from the USPTO upon request and payment of the fee set forth in 37 CFR 1.19(b)(3).

SEQUENCE LISTING

The patent contains a lengthy sequence listing. A copy of the sequence listing is available in electronic form from the USPTO web site (https://seqdata.uspto.gov/?pageRequest=docDetail&DocID=US11905563B2). An electronic copy of the sequence listing will also be available from the USPTO upon request and payment of the fee set forth in 37 CFR 1.19(b)(3).

What is claimed is:

1. A method of treating a cancer selected from the group consisting of colon adenocarcinoma (COAD), stomach adenocarcinoma (STAD), rectum adenocarcinoma (READ), esophageal carcinoma (ESCA), pancreatic adenocarcinoma (PAAD), and ovarian carcinoma (OV), said method comprising:
    isolating isomiRs or miRNAs from a sample obtained from the subject;
    characterizing the isomiRs or miRNAs and their presence or absence in the sample to identify a signature;
    evaluating the signature with a multi-cancer classifier, wherein the multi-cancer classifier has been trained using tumor samples from two or more cancers as examples and using qualitative, binarized profiles based on the presence or absence of expression of the isomiRs or miRNAs, wherein the "presence" of expression of the isomiR or miRNA means the isomiR or miRNA is among the top 20% most abundant isomiR or miRNA, and wherein the "absence" of expression of the isomiR or miRNA means the isomiR or miRNA is not among the top 20% most abundant isomiRs or miRNAs; and
    determining whether the signature is indicative of any one cancer of COAD, STAD, READ, ESCA, PAAD, or OV, among the two or more cancers; and
    administering to the subject a specific chemotherapy specifically targeting said any one cancer of COAD, STAD, READ, ESCA, PAAD, or OV being indicated.

2. The method of claim 1, wherein the sample is isolated from one or more cells, from tissue or from body fluid obtained from the subject.

3. The method of claim 2, wherein the sample is contained in a formalin-treated paraffin-embedded block.

4. The method of claim 2, wherein the sample is contained in an optimal cutting compound block.

5. The method of claim 2, wherein the body fluid is selected from the group consisting of amniotic fluid, aqueous humour and vitreous humour, bile, blood serum, breast milk, cerebrospinal fluid, cerumen, chyle, chyme, endolymph and perilymph, exudates, feces, female ejaculate, gastric acid, gastric juice, lymph, mucus, pericardial fluid, peritoneal fluid, pleural fluid, pus, rheum, saliva, sebum, serous fluid, semen, smegma, sputum, synovial fluid, sweat, tears, urine, vaginal secretion, and vomit.

6. The method of claim 2, wherein the sample is selected from the group consisting of a peripheral blood cell, a tumor cell, a circulating tumor cell, an exosome.

7. The method of claim 1, wherein the isomiRs are isolated by a method selected from the group consisting of size selection, amplification and sequencing.

8. The method of claim 1, wherein the miRNAs are isolated by a method selected from the group consisting of size selection, amplification and sequencing.

9. The method of claim 1, wherein isomiRs with a length in the range of 15 nucleotides to 25 nucleotides are isolated.

10. The method of claim 1, wherein miRNAs with a length in the range of 15 nucleotides to 25 nucleotides are isolated.

11. The method of claim 1, wherein the signature is obtained through sequence-specific methods that preserve the nucleotide sequence identity of at least one terminus of the isomiR.

12. The method of claim 1, wherein the signature is obtained through sequence-specific methods that preserve the nucleotide sequence identity of both termini of the isomiR.

13. The method of claim 1, wherein the signature is obtained by hybridization to an oligonucleotide panel of oligonucleotide probes.

14. The method of claim 13, wherein the oligonucleotide panel comprises at least one or more polynucleotide probes that selectively hybridize to at least one isomiR.

15. The method of claim 13, wherein the oligonucleotide panel comprises at least one or more polynucleotide probes that selectively hybridize to at least one miRNA.

16. The method of claim 1, wherein the abundance of the isolated isomiRs is not taken into account by subsequent analyses.

17. The method of claim 1, wherein the abundance of the isolated miRNAs is not taken into account by subsequent analyses.

18. The method of claim 1 wherein the tumor samples used to train the classifier are from two or more cancers selected from the group consisting of acute myeloid leukemia, adrenocortical carcinoma, bladder urothelial carcinoma, brain lower grade glioma, breast invasive carcinoma, cervical squamous cell carcinoma and endocervical adenocarcinoma, cholangiocarcinoma, colon adenocarcinoma, esophageal carcinoma, glioblastoma multiforme, head and neck squamous cell carcinoma, kidney chromophobe, kidney renal clear cell carcinoma, kidney renal papillary cell carcinoma, liver hepatocellular carcinoma, lung adenocarcinoma, lung squamous cell carcinoma, lymphoid neoplasm diffuse large b-cell lymphoma, mesothelioma, ovarian serous cystadenocarcinoma, pancreatic adenocarcinoma, pheochromocytoma and paraganglioma, prostate adenocarcinoma, rectum adenocarcinoma, sarcoma, skin cutaneous melanoma, stomach adenocarcinoma, testicular germ cell tumors, thymoma, thyroid carcinoma, uterine carcinosarcoma, uterine corpus endometrial carcinoma, and uveal melanoma.

19. The method of claim 18 wherein the classifier was trained specifically using as positive examples samples from one or more of stomach adenocarcinoma, colon adenocarcinoma, esophageal carcinoma, pancreatic adenocarcinoma, rectum adenocarcinoma, and as negative examples disease-free samples or samples from non-cancer diseases or samples from cancers other than stomach adenocarcinoma, colon adenocarcinoma, esophageal carcinoma, pancreatic adenocarcinoma, and rectum adenocarcinoma.

20. The method of claim 19, wherein the classifier uses features that are based on knowledge of the presence or absence of expression of miRNA arms.

21. The method of claim 20, wherein the total number of miRNA arms evaluated is between 1 and 161.

22. The method of claim 21, wherein the miRNAs to be evaluated are the ones with identifiers SEQ ID NOs 8,435 through 8,595 inclusive.

23. The method of claim 20, wherein the total number of miRNA arms evaluated is between 1 and 80.

24. The method of claim 23, wherein the miRNAs to be evaluated are the ones with identifiers SEQ ID NOs 8,435 through 8,514 inclusive.

25. The method of claim 20, wherein the total number of miRNA arms evaluated is between 1 and 40.

26. The method of claim 25, wherein the miRNAs to be evaluated are the ones with identifiers SEQ ID NOs 8,435 through 8,474 inclusive.

27. The method of claim 20, wherein the total number of miRNA arms evaluated is between 1 and 24.

28. The method of claim 27, wherein the miRNAs to be evaluated are the ones with identifiers SEQ ID NOs 8,435 through 8,458 inclusive.

29. The method of claim 20, wherein the total number of miRNA arms evaluated is between 1 and 16.

30. The method of claim 29, wherein the miRNAs to be evaluated are the ones with identifiers SEQ ID NOs 8,435 through 8,450 inclusive.

31. The method of claim 19 wherein the classifier was trained with positive examples that correspond solely to stomach adenocarcinoma.

32. The method of claim 31, wherein the classifier uses features that are based on knowledge of the presence or absence of expression of miRNA arms.

33. The method of claim 32 wherein the total number of miRNA arms evaluated is between 1 and 161.

34. The method of claim 33, wherein the miRNAs to be evaluated are the ones with identifiers SEQ ID NOs 8,274 through 8,434 inclusive.

35. The method of claim 32 wherein the total number of miRNA arms evaluated is between 1 and 80.

36. The method of claim 35, wherein the miRNAs to be evaluated are the ones with identifiers SEQ ID NOs 8,274 through 8,353 inclusive.

37. The method of claim 32 wherein the total number of miRNA arms evaluated is between 1 and 40.

38. The method of claim 37, wherein the miRNAs to be evaluated are the ones with identifiers SEQ ID NOs 8,274 through 8,313 inclusive.

39. The method of claim 32 wherein the total number of miRNA arms evaluated is between 1 and 24.

40. The method of claim 39, wherein the miRNAs to be evaluated are the ones with identifiers SEQ ID NOs 8,274 through 8,297 inclusive.

41. The method of claim 32 wherein the total number of miRNA arms evaluated is between 1 and 16.

42. The method of claim 41, wherein the miRNAs to be evaluated are the ones with identifiers SEQ ID NOs 8,274 through 8,289 inclusive.

43. The method of claim 1, wherein the total number of isomiRs evaluated is between 1 and 7,466.

44. The method of claim 43, wherein the isomiRs to be evaluated are the ones with identifiers SEQ ID NOs 1 through 7,466 inclusive.

45. The method of claim 1, wherein the total number of isomiRs evaluated is between 1 and 2,588.

46. The method of claim 45, wherein the isomiRs to be evaluated are the ones with identifiers SEQ ID NOs 1 through 2,588 inclusive.

47. The method of claim 1, wherein the total number of isomiRs evaluated is between 1 and 1,883.

48. The method of claim 47, wherein the isomiRs to be evaluated are the ones with identifiers SEQ ID NOs 1 through 1,883 inclusive.

49. The method of claim 1, wherein the total number of isomiRs evaluated is between 1 and 1,147.

50. The method of claim 49, wherein the isomiRs to be evaluated are the ones with identifiers SEQ ID NOs 1 through 1,147 inclusive.

51. The method of claim 1, wherein the total number of isomiRs evaluated is between 1 and 456.

52. The method of claim 51, wherein the isomiRs to be evaluated are the ones with identifiers SEQ ID NOs 1 through 456 inclusive.

53. The method of claim 1, wherein the total number of miRNA arms evaluated is between 1 and 807.

54. The method of claim 53, wherein the miRNAs to be evaluated are the ones with identifiers SEQ ID NOs 7,467 through 8,273 inclusive.

55. The method of claim 1, wherein the total number of miRNA arms evaluated is between 1 and 285.

56. The method of claim 55, wherein the isomiRs to be evaluated are the ones with identifiers SEQ ID NOs 7,467 through 7,751 inclusive.

57. The method of claim 1, wherein the total number of miRNA arms evaluated is between 1 and 198.

58. The method of claim 57, wherein the isomiRs to be evaluated are the ones with identifiers SEQ ID NOs 7,467 through 7,664 inclusive.

59. The method of claim 1, wherein the total number of miRNA arms evaluated is between 1 and 115.

60. The method of claim 59, wherein the isomiRs to be evaluated are the ones with identifiers SEQ ID NOs 7,467 through 7,581 inclusive.

61. The method of claim 1, wherein the total number of miRNA arms evaluated is between 1 and 47.

62. The method of claim 61, wherein the isomiRs to be evaluated are the ones with identifiers SEQ ID NOs 7,467 through 7,513 inclusive.

* * * * *